United States Patent
Park et al.

(10) Patent No.: US 11,676,706 B2
(45) Date of Patent: Jun. 13, 2023

(54) MEDICAL IMAGE PROCESSING APPARATUS AND MEDICAL IMAGE PROCESSING METHOD WHICH ARE FOR MEDICAL NAVIGATION DEVICE

(71) Applicant: GMEDITEC CO., LTD., Incheon (KR)

(72) Inventors: Jonghyun Park, Gyeonggi-do (KR); Dongpyo Seol, Gyeonggi-do (KR)

(73) Assignee: GMEDITEC CO., LTD., Incheon (KR)

( * ) Notice: Subject to any disclaimer, the term of this patent is extended or adjusted under 35 U.S.C. 154(b) by 0 days.

(21) Appl. No.: 17/513,884

(22) Filed: Oct. 29, 2021

(65) Prior Publication Data

US 2022/0051786 A1 Feb. 17, 2022

Related U.S. Application Data

(63) Continuation of application No. 16/807,139, filed on Mar. 2, 2020, now Pat. No. 11,183,295, which is a
(Continued)

(51) Int. Cl.
*G16H 30/40* (2018.01)
*G16H 30/20* (2018.01)
(Continued)

(52) U.S. Cl.
CPC .......... *G16H 30/40* (2018.01); *G06T 11/008* (2013.01); *G06T 15/06* (2013.01); *G06T 15/08* (2013.01);
(Continued)

(58) Field of Classification Search
CPC ...... G16H 30/40; G16H 30/20; G06T 11/008; G06T 15/06; G06T 15/08; G06T 2210/41;
(Continued)

(56) References Cited

U.S. PATENT DOCUMENTS 4,782,501 A 11/1988 Dixon, Jr.
5,442,733 A 8/1995 Kaufman et al.
(Continued)

FOREIGN PATENT DOCUMENTS

JP 2002-510230 4/2002
JP 2003-79637 3/2003
(Continued)

OTHER PUBLICATIONS

Xiaohui Yuan and G. Chi-Fishman, "Volumetric tongue reconstruction by fusing bidirectional MR images," 3rd IEEE International Symposium on Biomedical Imaging: Nano to Macro, 2006., 2006, pp. 1352-1355, doi: 10.1109/ISBI.2006.1625177. (Year: 2006).*
(Continued)

*Primary Examiner* — Charles L Beard
(74) *Attorney, Agent, or Firm* — Ladas & Parry, LLP

(57) ABSTRACT

The present invention relates to a medical image processing apparatus and a medical image processing method for a medical navigation device, and more particularly, to an apparatus and method for processing an image provided when using the medical navigation device. To this end, the present invention provides a medical image processing apparatus for a medical navigation device, including: a position tracking unit configured to obtain position information of the medical navigation device within an object; a memory configured to store medical image data generated based on a medical image of the object; and a processor configured to set a region of interest (ROI) based on position information of the medical navigation device in reference to the medical image data, and generate partial medical image data corresponding to the ROI, and a medical image processing method using the same.

14 Claims, 10 Drawing Sheets

Related U.S. Application Data continuation of application No. PCT/KR2017/009541, filed on Aug. 31, 2017.

(51) Int. Cl.
| | | |
|---|---|---|
| *G06T 11/00* | (2006.01) | |
| *G06T 15/06* | (2011.01) | |
| *G06T 15/08* | (2011.01) | |
| *G06V 10/24* | (2022.01) | |

(52) U.S. Cl.
CPC ............. *G06V 10/24* (2022.01); *G16H 30/20* (2018.01); *G06T 2210/41* (2013.01); *G06T 2211/428* (2013.01); *G06T 2215/16* (2013.01)

(58) Field of Classification Search
CPC .......... G06T 2211/428; G06T 2215/16; G06V 10/24
See application file for complete search history.

(56) References Cited

U.S. PATENT DOCUMENTS

| | | | | |
|---|---|---|---|---|
| 5,555,352 | A | 9/1996 | Lucas | |
| 5,630,034 | A | 5/1997 | Oikawa et al. | |
| 6,166,742 | A | 12/2000 | He | |
| 7,085,400 | B1 | 8/2006 | Holsing et al. | |
| 7,091,973 | B1* | 8/2006 | Cohen ................... G06T 15/50 345/426 |
| 7,330,578 | B2* | 2/2008 | Wang ................... G06T 15/08 345/419 |
| 7,952,583 | B2 | 5/2011 | Waechter et al. | |
| 8,780,115 | B1* | 7/2014 | Mackrell ............ G06Q 30/0241 345/440.1 |
| 8,867,807 | B1* | 10/2014 | Fram ................... G16H 30/20 382/128 |
| 9,072,470 | B2 | 7/2015 | Sumi et al. | |
| 9,245,377 | B1* | 1/2016 | Jarosz ................... G06T 15/55 |
| 9,256,978 | B2 | 2/2016 | Kim et al. | |
| 9,280,848 | B1* | 3/2016 | Chen ................... G06T 15/506 |
| 9,495,794 | B2 | 11/2016 | Masumoto | |
| 9,633,413 | B2* | 4/2017 | Kim ................... G09G 3/035 |
| 9,706,972 | B1 | 7/2017 | Ahn et al. | |
| 9,799,135 | B2 | 10/2017 | Zhou et al. | |
| 10,354,438 | B2 | 7/2019 | Engel et al. | |
| 10,467,752 | B2* | 11/2019 | Tanji ................... A61B 34/10 |
| 10,546,415 | B2 | 1/2020 | Petkov et al. | |
| 10,565,773 | B1* | 2/2020 | Tytgat ................... G06T 15/005 |
| 10,573,067 | B1* | 2/2020 | Naik ................... H04N 5/2224 |
| 10,595,824 | B2 | 3/2020 | Kim | |
| 10,664,217 | B1* | 5/2020 | Laha ................... G06F 3/1423 |
| 10,671,237 | B2* | 6/2020 | McBeth ................... G06F 3/011 |
| 10,755,474 | B1* | 8/2020 | Schneider ............ G06T 15/506 |
| 10,790,056 | B1* | 9/2020 | Accomazzi ............ G16H 40/20 |
| 10,799,101 | B2 | 10/2020 | Nakamura et al. | |
| 11,398,072 | B1* | 7/2022 | Schneider ................ G06T 15/08 |
| 2002/0005850 | A1* | 1/2002 | Osborne ................ G06T 15/08 345/424 |
| 2004/0046704 | A1* | 3/2004 | Kim ................... G06F 1/1601 345/1.1 |
| 2004/0070584 | A1* | 4/2004 | Pyo ................... G06T 11/006 345/419 |
| 2004/0228453 | A1* | 11/2004 | Dobbs ................... G01N 23/046 378/210 |
| 2006/0056726 | A1* | 3/2006 | Fujiwara ................ G06T 15/08 382/276 |
| 2006/0066611 | A1* | 3/2006 | Fujiwara ................ G06T 15/06 345/419 |
| 2006/0071930 | A1* | 4/2006 | Fujiwara ................ G06T 15/08 345/419 |
| 2006/0238534 | A1* | 10/2006 | Matsumoto ............. G06T 19/00 345/420 |
| 2006/0274065 | A1* | 12/2006 | Buyanovskiy ........ G06T 17/005 345/623 |
| 2006/0291705 | A1* | 12/2006 | Baumann ................ G06T 15/08 382/128 |
| 2007/0009078 | A1* | 1/2007 | Saito ................... G06T 15/06 378/4 |
| 2007/0098299 | A1* | 5/2007 | Matsumoto ............ G06T 15/08 382/284 |
| 2007/0167801 | A1* | 7/2007 | Webler ................... G06T 19/00 600/459 |
| 2007/0247460 | A1* | 10/2007 | Smitt ................... G06T 15/50 345/427 |
| 2007/0248259 | A1 | 10/2007 | Liu | |
| 2007/0265813 | A1* | 11/2007 | Unai ................... G06T 7/12 703/2 |
| 2007/0285421 | A1* | 12/2007 | Kobayashi ............ A61B 8/00 345/424 |
| 2007/0299639 | A1 | 12/2007 | Weese et al. | |
| 2008/0084542 | A1* | 4/2008 | Lalley ................... G03B 21/10 353/121 |
| 2008/0123912 | A1* | 5/2008 | Lal ........................ G06T 7/194 382/128 |
| 2008/0246768 | A1 | 10/2008 | Murray et al. | |
| 2008/0259080 | A1* | 10/2008 | Masumoto ............. G06T 15/08 345/426 |
| 2009/0003668 | A1 | 1/2009 | Matsumoto | |
| 2009/0060309 | A1* | 3/2009 | Tsujii ................... G06T 15/08 382/131 |
| 2009/0096787 | A1* | 4/2009 | Masumoto ............ G06T 7/0012 382/131 |
| 2009/0097722 | A1* | 4/2009 | Dekel ................... G06T 15/08 382/128 |
| 2009/0128552 | A1* | 5/2009 | Fujiki ................... G06T 19/006 345/419 |
| 2009/0136096 | A1 | 5/2009 | Sirohey et al. | |
| 2009/0174729 | A1 | 7/2009 | Matsumoto | |
| 2009/0221920 | A1 | 9/2009 | Boppart et al. | |
| 2009/0226055 | A1* | 9/2009 | Dankowicz ............ G06T 7/0012 382/128 |
| 2009/0295805 | A1* | 12/2009 | Ha ........................ G06T 15/50 345/426 |
| 2010/0014737 | A1 | 1/2010 | Rührnschopf et al. | |
| 2010/0033482 | A1 | 2/2010 | Zhou et al. | |
| 2010/0245369 | A1* | 9/2010 | Yoshino ................ H04N 13/398 345/1.3 |
| 2010/0266184 | A1* | 10/2010 | Kitamura ............... G16H 30/40 382/131 |
| 2011/0032533 | A1 | 2/2011 | Izatt et al. | |
| 2011/0043613 | A1* | 2/2011 | Rohaly ................ G06V 20/653 348/E13.074 |
| 2011/0069069 | A1 | 3/2011 | Engel | |
| 2011/0102435 | A1* | 5/2011 | Brabec ................ G06T 15/08 345/424 |
| 2011/0137156 | A1* | 6/2011 | Razzaque ............ A61B 34/20 600/424 |
| 2011/0158386 | A1 | 6/2011 | Payne et al. | |
| 2011/0178394 | A1* | 7/2011 | Fitzpatrick ............. G06T 7/33 382/154 |
| 2011/0188726 | A1* | 8/2011 | Nathaniel ............ A61B 6/4441 378/42 |
| 2011/0231795 | A1* | 9/2011 | Cheon ................... G06F 1/3231 715/810 |
| 2011/0273667 | A1 | 11/2011 | Knighton et al. | |
| 2011/0292081 | A1* | 12/2011 | Matsunobu ............ G06F 3/1423 345/655 |
| 2012/0047465 | A1* | 2/2012 | Noda ................... G06F 3/0346 715/848 |
| 2012/0050277 | A1* | 3/2012 | Murakoshi ............ G06T 19/00 345/157 |
| 2012/0053408 | A1* | 3/2012 | Miyamoto ............ G06T 7/74 600/109 |
| 2012/0069020 | A1 | 3/2012 | Smith-Casern | |
| 2012/0139815 | A1* | 6/2012 | Aono ................... G06F 1/1616 345/1.3 |
| 2012/0242893 | A1* | 9/2012 | Akitomo ................ G06F 3/1446 348/E7.003 |
| 2012/0249742 | A1* | 10/2012 | Abert ................... G06T 11/203 348/46 |

(56) References Cited

U.S. PATENT DOCUMENTS

| | | | |
|---|---|---|---|
| 2012/0250961 A1* | 10/2012 | Iwasaki | G16H 15/00 382/128 |
| 2013/0002671 A1* | 1/2013 | Armsden | G06T 15/50 345/426 |
| 2013/0069970 A1* | 3/2013 | Sasaki | G06T 15/06 345/589 |
| 2013/0076677 A1* | 3/2013 | Kretz | H04N 5/2628 345/1.3 |
| 2013/0120385 A1* | 5/2013 | Krishnaswamy | G06T 15/50 345/426 |
| 2013/0139105 A1* | 5/2013 | Park | G06F 3/0481 715/781 |
| 2013/0222276 A1* | 8/2013 | Kim | G06F 1/1643 345/173 |
| 2014/0005530 A1* | 1/2014 | Liu | A61B 8/085 600/443 |
| 2014/0071132 A1* | 3/2014 | Noshi | A61B 6/022 345/427 |
| 2014/0079178 A1* | 3/2014 | Mukumoto | G06T 11/008 378/4 |
| 2014/0132597 A1* | 5/2014 | Tsukagoshi | G06T 7/33 345/419 |
| 2014/0139518 A1* | 5/2014 | Kim | A61B 8/523 345/419 |
| 2014/0152560 A1* | 6/2014 | Hussain | G06F 3/04883 345/158 |
| 2014/0205150 A1* | 7/2014 | Ogawa | G01B 11/14 382/106 |
| 2014/0267271 A1* | 9/2014 | Billeter | G06T 15/005 345/426 |
| 2014/0342823 A1 | 11/2014 | Kapulkin et al. | |
| 2014/0354695 A1* | 12/2014 | Sakai | G09G 5/00 345/650 |
| 2015/0063545 A1 | 3/2015 | Lee et al. | |
| 2015/0093005 A1 | 4/2015 | Oh et al. | |
| 2015/0145892 A1* | 5/2015 | Hong | G06F 3/1446 345/649 |
| 2015/0154790 A1* | 6/2015 | Kim | G06T 15/50 345/424 |
| 2015/0161802 A1* | 6/2015 | Christiansen | A61B 5/1076 348/74 |
| 2015/0164475 A1* | 6/2015 | Kuga | A61B 8/463 600/443 |
| 2015/0193187 A1* | 7/2015 | Kimn | G09G 5/006 345/1.2 |
| 2015/0205565 A1* | 7/2015 | Koguchi | G09G 3/2088 345/1.3 |
| 2015/0208039 A1* | 7/2015 | Kuga | A61B 6/5211 348/46 |
| 2015/0227298 A1* | 8/2015 | Kim | G06F 3/04845 715/799 |
| 2015/0228110 A1* | 8/2015 | Hecht | G06T 15/50 345/419 |
| 2015/0243055 A1* | 8/2015 | Nishiyama | G06T 19/20 382/131 |
| 2015/0262416 A1 | 9/2015 | Hecht | |
| 2015/0262422 A1 | 9/2015 | Znamenskiy et al. | |
| 2015/0293739 A1* | 10/2015 | Choi | G06F 3/038 345/157 |
| 2015/0302638 A1* | 10/2015 | Jago | A61B 8/0866 345/420 |
| 2015/0317026 A1* | 11/2015 | Choi | G06F 3/0481 345/660 |
| 2015/0348314 A1* | 12/2015 | Koguchi | G06T 15/506 345/420 |
| 2015/0379780 A1* | 12/2015 | Jin | A61B 6/032 345/419 |
| 2016/0018663 A1* | 1/2016 | Kim | G02B 30/50 359/479 |
| 2016/0030007 A1 | 2/2016 | Tsujita | |
| 2016/0038248 A1* | 2/2016 | Bharadwaj | A61B 90/10 715/771 |
| 2016/0042559 A1* | 2/2016 | Seibert | G06T 15/506 345/426 |
| 2016/0070436 A1* | 3/2016 | Thomas | A61B 8/0808 715/771 |
| 2016/0080719 A1* | 3/2016 | Tsukagoshi | H04N 13/341 348/46 |
| 2016/0098820 A1* | 4/2016 | Rousselle | G06T 5/002 345/426 |
| 2016/0133042 A1 | 5/2016 | Kim | |
| 2016/0135775 A1* | 5/2016 | Mistretta | G06T 7/0012 600/419 |
| 2016/0148401 A1* | 5/2016 | Hirai | A61N 5/107 600/1 |
| 2016/0162244 A1* | 6/2016 | Christmas | G06T 15/00 345/1.3 |
| 2016/0163045 A1* | 6/2016 | Penney | G06T 15/20 382/131 |
| 2016/0171753 A1* | 6/2016 | Park | G06T 15/50 345/420 |
| 2016/0203602 A1* | 7/2016 | Hayashi | G06V 10/143 382/128 |
| 2016/0260222 A1 | 9/2016 | Paglieroni et al. | |
| 2016/0269723 A1* | 9/2016 | Zhou | G06T 5/002 |
| 2016/0275679 A1* | 9/2016 | Im | G06T 11/003 |
| 2016/0343161 A1 | 11/2016 | Paladini et al. | |
| 2016/0350963 A1* | 12/2016 | Petkov | G06T 15/06 |
| 2017/0046858 A1 | 2/2017 | Brokish et al. | |
| 2017/0061675 A1* | 3/2017 | Segasby | G06T 19/20 |
| 2017/0061681 A1* | 3/2017 | Engel | G06T 15/06 |
| 2017/0084059 A1* | 3/2017 | Hagiwara | G06T 11/008 |
| 2017/0124770 A1 | 5/2017 | Vats | |
| 2017/0140527 A1* | 5/2017 | Govari | A61B 6/037 |
| 2017/0150874 A1 | 6/2017 | Kawano et al. | |
| 2017/0161909 A1 | 6/2017 | Hamanaka et al. | |
| 2017/0178390 A1 | 6/2017 | Ye et al. | |
| 2017/0186216 A1* | 6/2017 | Engel | G06T 15/06 |
| 2017/0193690 A1* | 7/2017 | Ha | G06T 15/80 |
| 2017/0199627 A1* | 7/2017 | Ikeda | G06F 21/84 |
| 2017/0206861 A1* | 7/2017 | Rojas | G06F 3/04883 |
| 2017/0228918 A1* | 8/2017 | Ovtchinnikov | G06F 3/04815 |
| 2017/0236325 A1* | 8/2017 | Lecocq | G06T 15/55 345/426 |
| 2017/0236492 A1* | 8/2017 | Taki | G06F 3/048 345/428 |
| 2017/0248532 A1 | 8/2017 | Kadambi et al. | |
| 2017/0249749 A1* | 8/2017 | Takahashi | A61B 5/7435 |
| 2017/0255340 A1* | 9/2017 | Ishii | G09G 5/14 |
| 2017/0255374 A1* | 9/2017 | Yasuda | G09G 5/14 |
| 2017/0262250 A1* | 9/2017 | Tanabe | G09G 3/001 |
| 2017/0294042 A1 | 10/2017 | Engel | |
| 2017/0309061 A1 | 10/2017 | Wang et al. | |
| 2017/0312031 A1* | 11/2017 | Amanatullah | A61B 34/10 |
| 2017/0323432 A1 | 11/2017 | Funabasama et al. | |
| 2017/0323471 A1* | 11/2017 | Chien | G06T 15/60 |
| 2017/0339394 A1* | 11/2017 | Paulus, Jr. | H04N 23/69 |
| 2017/0358123 A1 | 12/2017 | Novak et al. | |
| 2017/0364249 A1* | 12/2017 | Kumaki | H01Q 13/10 |
| 2018/0039470 A1* | 2/2018 | Tokita | G06F 3/1423 |
| 2018/0055575 A1* | 3/2018 | Krimsky | A61B 34/20 |
| 2018/0061111 A1* | 3/2018 | Engel | G06T 15/08 |
| 2018/0061370 A1* | 3/2018 | Ota | H04N 9/3147 |
| 2018/0082487 A1 | 3/2018 | Kiraly et al. | |
| 2018/0092615 A1* | 4/2018 | Sakaguchi | G16B 5/00 |
| 2018/0103246 A1* | 4/2018 | Yamamoto | A61B 1/04 |
| 2018/0107440 A1* | 4/2018 | Knoppert | G06F 3/147 |
| 2018/0137244 A1 | 5/2018 | Sorenson et al. | |
| 2018/0143796 A1* | 5/2018 | Murakawa | G06F 3/1431 |
| 2018/0150110 A1* | 5/2018 | Tokuchi | G06F 3/0488 |
| 2018/0158217 A1 | 6/2018 | Wang et al. | |
| 2018/0173373 A1* | 6/2018 | Hill | G06F 3/0481 |
| 2018/0174354 A1* | 6/2018 | Dufay | G06T 15/506 |
| 2018/0176506 A1* | 6/2018 | McNelley | H04N 7/142 |
| 2018/0189014 A1* | 7/2018 | Patil | G06F 3/1446 |
| 2018/0225861 A1* | 8/2018 | Petkov | G06T 15/06 |
| 2018/0239305 A1* | 8/2018 | Shi | G03H 1/0841 |
| 2018/0240213 A1* | 8/2018 | Izumi | G06T 3/0006 |
| 2018/0260995 A1 | 9/2018 | Steen | |
| 2018/0260997 A1 | 9/2018 | Petkov et al. | |

(56) References Cited

U.S. PATENT DOCUMENTS

| | | | |
|---|---|---|---|
| 2018/0267326 A1* | 9/2018 | Broadbent | G02B 30/50 |
| 2018/0308264 A1 | 10/2018 | Gu et al. | |
| 2018/0308278 A1 | 10/2018 | Qiu et al. | |
| 2018/0322806 A1 | 11/2018 | Avisar et al. | |
| 2018/0329580 A1* | 11/2018 | Aurongzeb | G09G 3/035 |
| 2018/0329609 A1* | 11/2018 | De Swarte | G06T 19/00 |
| 2018/0330520 A1* | 11/2018 | Brücker | G06T 7/80 |
| 2018/0330538 A1 | 11/2018 | Petkov | |
| 2018/0333129 A1 | 11/2018 | Toepfer | |
| 2018/0342074 A1* | 11/2018 | Sakamoto | G06T 7/55 |
| 2018/0350129 A1 | 12/2018 | Assmann et al. | |
| 2018/0357032 A1* | 12/2018 | Popovich | H04L 12/1813 |
| 2018/0360408 A1* | 12/2018 | Quan | G06T 7/70 |
| 2019/0000588 A1 | 1/2019 | Choudhry et al. | |
| 2019/0005611 A1* | 1/2019 | Aguirre-Valencia | G16H 30/20 |
| 2019/0005612 A1* | 1/2019 | Aguirre-Valencia | G06T 19/20 |
| 2019/0015163 A1* | 1/2019 | Abhari | H04N 7/181 |
| 2019/0021699 A1* | 1/2019 | Bracken | A61B 6/4417 |
| 2019/0029784 A1 | 1/2019 | Moalem et al. | |
| 2019/0042066 A1* | 2/2019 | Kim | H04M 1/725 |
| 2019/0043449 A1* | 2/2019 | Niinuma | G09G 5/12 |
| 2019/0065134 A1* | 2/2019 | Kanki | G09G 5/00 |
| 2019/0066391 A1 | 2/2019 | Anderso et al. | |
| 2019/0130630 A1 | 5/2019 | Ackerson et al. | |
| 2019/0133693 A1* | 5/2019 | Mahfouz | A61B 5/11 |
| 2019/0141315 A1* | 5/2019 | Broadbent | H04N 13/39 |
| 2019/0146653 A1* | 5/2019 | Ikuta | G06F 3/01 715/863 |
| 2019/0147639 A1* | 5/2019 | Sudarsky | A61B 5/1073 345/424 |
| 2019/0147645 A1* | 5/2019 | Mory | G06T 15/50 600/443 |
| 2019/0150745 A1 | 5/2019 | Sobek et al. | |
| 2019/0156526 A1 | 5/2019 | Liu et al. | |
| 2019/0164345 A1 | 5/2019 | Petkov et al. | |
| 2019/0167370 A1* | 6/2019 | Olson | G06F 3/03545 |
| 2019/0179968 A1* | 6/2019 | Iwadate | G09G 5/14 |
| 2019/0200951 A1* | 7/2019 | Meier | A61B 8/54 |
| 2019/0220172 A1* | 7/2019 | Sakashita | G06F 9/44 |
| 2019/0221027 A1* | 7/2019 | Petkov | G06T 15/06 |
| 2019/0239926 A1* | 8/2019 | Pavlovskaia | B33Y 80/00 |
| 2019/0247130 A1* | 8/2019 | State | G06T 19/003 |
| 2019/0272027 A1 | 9/2019 | Löffler et al. | |
| 2019/0272631 A1 | 9/2019 | Shemonski et al. | |
| 2019/0272667 A1* | 9/2019 | Roundhill | G06T 15/08 |
| 2019/0295497 A1* | 9/2019 | Itakura | G06F 3/0425 |
| 2019/0304129 A1* | 10/2019 | Schafer | A61B 1/00009 |
| 2019/0306467 A1* | 10/2019 | Sonoda | A61B 1/00 |
| 2019/0311530 A1* | 10/2019 | Wahrenberg | G06T 7/0012 |
| 2019/0318534 A1* | 10/2019 | Mory | A61B 8/4483 |
| 2019/0320886 A1* | 10/2019 | Yano | G02B 23/2461 |
| 2019/0325573 A1* | 10/2019 | Bernard | A61B 6/469 |
| 2019/0340837 A1* | 11/2019 | Shmayahu | G06T 17/00 |
| 2019/0340838 A1* | 11/2019 | Gluhovsky | G06T 19/00 |
| 2019/0362150 A1* | 11/2019 | Wei | G06V 20/20 |
| 2019/0378607 A1* | 12/2019 | Chen | G16H 30/40 |
| 2019/0388123 A1* | 12/2019 | Pavlovskaia | G06T 19/00 |
| 2020/0005520 A1 | 1/2020 | Zhang et al. | |
| 2020/0008770 A1* | 1/2020 | Salomon | A61B 6/5264 |
| 2020/0035348 A1* | 1/2020 | Sartor | G16H 30/20 |
| 2020/0036910 A1* | 1/2020 | Alzaga | G06T 7/70 |
| 2020/0041261 A1* | 2/2020 | Bernstein | A61B 1/00167 |
| 2020/0050550 A1* | 2/2020 | Muthler | G06T 1/60 |
| 2020/0054398 A1* | 2/2020 | Kovtun | G16H 40/63 |
| 2020/0105048 A1* | 4/2020 | Rust | G06T 15/506 |
| 2020/0105053 A1* | 4/2020 | Prakash | G06T 15/506 |
| 2020/0107886 A1* | 4/2020 | Govari | G06T 7/33 |
| 2020/0129237 A1 | 4/2020 | Ay et al. | |
| 2020/0183566 A1* | 6/2020 | Ouyang | G06T 11/40 |
| 2020/0193695 A1 | 6/2020 | Dingeldey | |
| 2020/0203006 A1* | 6/2020 | Park | G06V 10/24 |
| 2020/0205763 A1 | 7/2020 | Helm et al. | |
| 2020/0206536 A1* | 7/2020 | Wang | G06T 7/246 |
| 2020/0227000 A1* | 7/2020 | Liu | G06V 40/16 |
| 2020/0240934 A1* | 7/2020 | Yi | G06T 11/008 |
| 2020/0258314 A1* | 8/2020 | Nonoyama | G06F 3/016 |
| 2020/0264659 A1* | 8/2020 | Kim | G06F 3/0482 |
| 2020/0275977 A1* | 9/2020 | Govari | A61B 34/10 |
| 2020/0286225 A1* | 9/2020 | Ben-Haim | G06T 7/0012 |
| 2020/0289025 A1* | 9/2020 | Dichterman | A61B 5/063 |
| 2020/0293260 A1* | 9/2020 | Fitzgerald | H04N 21/42204 |
| 2020/0302683 A1 | 9/2020 | Huang | |
| 2020/0342653 A1 | 10/2020 | Dupuis et al. | |
| 2020/0357513 A1* | 11/2020 | Katra | G16H 40/67 |
| 2020/0367970 A1* | 11/2020 | Qiu | A61B 34/10 |
| 2020/0380680 A1 | 12/2020 | Aoyagi et al. | |
| 2020/0402236 A1* | 12/2020 | Courot | A61B 8/4416 |
| 2020/0402286 A1* | 12/2020 | Thienphrapa | A61B 5/6847 |
| 2020/0410727 A1* | 12/2020 | Yamakawa | G06T 11/008 |
| 2021/0004961 A1* | 1/2021 | Takahashi | A61B 1/00009 |
| 2021/0007715 A1* | 1/2021 | Belt | A61B 8/461 |
| 2021/0019932 A1 | 1/2021 | Breivik | |
| 2021/0035356 A1 | 2/2021 | Castaneda et al. | |
| 2021/0052919 A1* | 2/2021 | Ho | G16H 20/40 |
| 2021/0068742 A1* | 3/2021 | Goto | A61B 5/1079 |
| 2021/0072944 A1* | 3/2021 | Neldeborn | H04N 21/4781 |
| 2021/0074052 A1* | 3/2021 | Ha | G06T 15/005 |
| 2021/0090261 A1* | 3/2021 | Sugimoto | G06N 3/045 |
| 2021/0090325 A1* | 3/2021 | Engel | |
| 2021/0113857 A1 | 4/2021 | Maltz | |
| 2021/0121143 A1 | 4/2021 | Iniewski et al. | |
| 2021/0125396 A1 | 4/2021 | Martin et al. | |
| 2021/0132687 A1* | 5/2021 | Luo | G06F 3/011 |
| 2021/0236233 A1* | 8/2021 | Fuerst | A61B 1/000095 |
| 2021/0287454 A1* | 9/2021 | Shah | G16H 30/20 |
| 2021/0304423 A1* | 9/2021 | Yi | A61B 34/20 |
| 2021/0335031 A1* | 10/2021 | Hamilton | G06T 15/503 |
| 2021/0358198 A1* | 11/2021 | Pantaleoni | G06T 15/06 |
| 2021/0390757 A1* | 12/2021 | Muthler | G06T 15/06 |
| 2022/0005252 A1* | 1/2022 | Breivik | G06T 15/08 |
| 2022/0036641 A1* | 2/2022 | Vorba | G06T 15/506 |
| 2022/0122312 A1* | 4/2022 | Vega | G16H 30/40 |
| 2022/0130099 A1* | 4/2022 | Yang | G06T 15/506 |
| 2022/0172411 A1* | 6/2022 | Chelnokov | G06T 7/0012 |
| 2022/0180591 A1* | 6/2022 | Taskov | G06T 15/06 |
| 2022/0277507 A1* | 9/2022 | Park | G06T 19/20 |
| 2022/0284657 A1* | 9/2022 | Müller | G06N 3/084 |
| 2022/0287669 A1* | 9/2022 | Sudarsky | A61B 6/032 |
| 2022/0327762 A1* | 10/2022 | Panteleev | G06T 15/506 |
| 2022/0327765 A1* | 10/2022 | Liu | G06T 15/506 |
| 2022/0335636 A1* | 10/2022 | Bi | G06T 7/586 |

FOREIGN PATENT DOCUMENTS

| | | |
|---|---|---|
| JP | 2003-265408 | 9/2003 |
| JP | 2005-520590 | 7/2005 |
| JP | 2006-223894 | 8/2006 |
| JP | 2012-165838 | 9/2012 |
| JP | 2014-104328 | 6/2014 |
| KR | 10-2012-0122542 | 11/2012 |
| KR | 10-2014-0089222 | 7/2014 |
| KR | 10-2017-0026163 | 3/2017 |
| KR | 10-1728044 | 4/2017 |
| KR | 10-2017-0062897 | 6/2017 |
| WO | 2008/125910 | 10/2008 |
| WO | 2019/045144 | 3/2019 |

OTHER PUBLICATIONS

D. Yin and R.-W. Lu, "A Method of Breast Tumour MRI Segmentation and 3D Reconstruction," 2015 7th International Conference on Information Technology in Medicine and Education (ITME), 2015, pp. 23-26, doi: 10.1109/ITME.2015.117. (Year: 2015).*

N. Max, "Optical models for direct volume rendering," in IEEE Transactions on Visualization and Computer Graphics, vol. 1, No. 2, pp. 99-108, Jun. 1995, doi: 10.1109/2945.468400. (Year: 1995).*

International Search Report for PCT/KR2017/009541 dated May 10, 2018 and its English translation from WIPO (now published as WO 2019/045144).

Written Opinion of the International Searching Authority for PCT/KR2017/009541 dated May 10, 2018 and its English translation

(56) References Cited

OTHER PUBLICATIONS from WIPO (now published as WO 2019/045144).
Office Action dated May 4, 2018 for Korean Patent Application No. 10-2017-0110940 and its English translation provided by Applicant's foreign council.
Office Action dated Nov. 2, 2018 for Korean Patent Application No. 10-2017-0110940 and its English translation provided by Applicant's foreign council.
Notice of Allowance dated May 1, 2019 for Korean Patent Application No. 10-2017-0110940 and its English translation provided by Applicant's foreign council.
Office Action dated Mar. 12, 2019 for Korean Patent Application No. 10-2017-0110943 and its English translation provided by Applicant's foreign council.
Office Action dated Nov. 9, 2019 for Korean Patent Application No. 10-2017-0110943 and its English translation provided by Applicant's foreign council.
Notice of Allowance dated Feb. 2, 2020 for Korean Patent Application No. 10-2017-0110943 and its English translation provided by Applicant's foreign council.
Notice of Allowance dated Jul. 22, 2021 for U.S. Appl. No. 16/807,139 (now published as US 2020/0203006).
Office Action dated Apr. 15, 2021 for U.S. Appl. No. 16/807,139 (now published as US 2020/0203006).

* cited by examiner

*Prior Art*

(a)          (b)

MEDICAL IMAGE PROCESSING APPARATUS AND MEDICAL IMAGE PROCESSING METHOD WHICH ARE FOR MEDICAL NAVIGATION DEVICE

CROSS-REFERENCE TO RELATED APPLICATIONS

This application is a continuation of U.S. patent application Ser. No. 16/807,139 filed on Mar. 2, 2020, which is a continuation of International Patent Application No. PCT/KR2017/009541 filed on Aug. 31, 2017, the entire contents of which are incorporated herein by reference.

TECHNICAL FIELD

The present invention relates to a medical image processing apparatus and a medical image processing method for a medical navigation device, and more particularly, to an apparatus and method for processing an image provided when using the medical navigation device.

BACKGROUND ART

A minimally invasive surgery that minimizes the incision site of the patient during surgery is widely used. The minimally invasive surgery has an advantage of minimizing the incision and thus minimizing blood loss and recovery time, but restricts the doctor's field of view thus having some risk factors such as meninx damage and eye damage in some surgeries. As a tool for overcoming the disadvantages of minimally invasive surgery in which the doctor's field of view of is restricted, a medical navigation device (or surgical navigation device) is used. The medical navigation device tracks in real time the position of the instrument in the surgical site in reference to a previously obtained medical image of the patient. In addition, such a medical navigation device may be used in combination with an endoscope.

An optical or electromagnetic position tracking devices may be used for real-time position tracking of the inserted surgical instrument in the medical navigation device. As an example for tracking the position of the surgical instrument, an optical position tracking device including an infrared emitting device and a passive image sensor may be used. The optical position tracking device emits reference light through the infrared emitting device and collects the image reflected by plural markers through the image sensor. The position tracking apparatus may obtain position information of the surgical instrument based on the positions of the markers. Meanwhile, as another example for tracking the position of the surgical instrument, an electromagnetic position tracking device including a magnetic field generator and a conductive metal object may be used. The electromagnetic position tracking device may obtain the position information of the surgical instrument by measuring the eddy current occurs in the conductive metal object in the magnetic field generated by the magnetic field generator. In order to accurately indicate the positional relationship between the surgical instrument and the body part in the position tracking device, a registration process may be required that defines the initial positional relationship between the medical data for the patient's body part and the surgical instrument.

FIG. 1 illustrates an embodiment of an output image of a medical navigation device. The medical navigation device may display at least one of horizontal, sagittal, and coronal images of a body part. The operator (or doctor) interprets each image to determine the three-dimensional position of the surgical instrument, and to identify adjacent risk factors. However, these cross-sectional images are not intuitive representation of the position of the surgical instrument in surgical site. Therefore, in order to identify the exact position of the surgical instrument with cross-sectional images, the operator may need a lot of time as well as a skill. In addition, when the time of looking at the monitor of the medical navigation device to determine the position of the surgical instrument is prolonged, the overall surgery time becomes long, which may increase the fatigue of both the operator and the patient.

DISCLOSURE

Technical Problem

The present invention has an object to provide a medical image processing method for helping the operator to intuitively identify information on surgical site and adjacent elements (e.g. organs) in a patient's body.

In addition, the present invention has an object to effectively render the medical image of the patient taken in advance and the intraoperative image in surgical site.

In addition, the present invention has an object to provide a medical navigation device that is easy to identify the patient's anatomical structure.

Technical Solution

In order to solve the above problems, the present invention provides a medical image processing apparatus and a medical image processing method as follows.

First, an exemplary embodiment of the present invention provides a medical image processing apparatus using an augmented reality, including: an endoscopic image obtaining unit which obtains an endoscopic image of an object; a memory which stores medical image data generated based on a medical image of the object; and a processor which obtains position and direction information of the endoscope in reference to the medical image data, determines a target area to be displayed in augmented reality among the medical image data based on the obtained position and direction information, and renders partial medical image data corresponding to the target area as an augmented reality image on the endoscopic image.

In addition, an exemplary embodiment of the present invention provides a medical image processing method using an augmented reality, including: obtaining an endoscopic image of an object; obtaining position and direction information of the endoscope in reference to medical image data of the object, wherein the medical image data of the object is generated based on a medical image of the object; determining a target area to be displayed in augmented reality among the medical image data based on the obtained position and direction information; and rendering partial medical image data corresponding to the target area as an augmented reality image on the endoscopic image.

According to an embodiment, the medical image data may include data obtained by synthesizing the medical image of the object and user defined auxiliary data and performing volume rendering on the synthesized data.

In this case, the auxiliary data may be represented as a voxel having a value outside a pre-defined Hounsfield Unit (HU) range.

In addition, the range outside pre-defined HU range may include a first HU range exceeding a first threshold and a second HU range below a second threshold, and a value of the first HU range and a value of the second HU range may represent different types of auxiliary data.

According to an embodiment, the pre-defined HU range may reach from −1000 HU to +1000 HU.

According to another embodiment of the present invention, the processor may generate a first normal map using the endoscopic image, and obtain the position and direction information of the endoscope in reference to the medical image data based on a result of determining a similarity between the first normal map with a plurality of second normal maps obtained from the medical image data.

In this case, the processor may compare the first normal map with second normal maps within a preset range from a position and a direction of the endoscope at a previous time point.

According to an embodiment, the first normal map may be obtained based on reflection information of structured light with respect to a search area of the object.

In addition, the second normal map may be obtained from the medical image data based on position and direction information of a virtual endoscope for the object.

In addition, the direction information of the virtual endoscope may be determined based on a straight line connecting a start point (or a previous position) of a path of the virtual endoscope and a current position of the virtual endoscope.

Next, another exemplary embodiment of the present invention provides a medical image processing apparatus for a medical navigation device, including: a position tracking unit which obtains position information of the medical navigation device within an object; a memory which stores medical image data generated based on a medical image of the object; and a processor which sets a region of interest (ROI) based on position information of the medical navigation device in reference to the medical image data, and generates partial medical image data corresponding to the ROI.

In addition, another exemplary embodiment of the present invention provides a medical image processing method for a medical navigation device, including: obtaining position information of the medical navigation device within an object; storing medical image data generated based on a medical image of the object; setting a region of interest (ROI) based on position information of the medical navigation device in reference to the medical image data; and generating partial medical image data corresponding to the ROI.

In this case, the ROI may be set based on an area within a preset distance from a position of the medical navigation device in reference to at least one of a horizontal plane, a sagittal plane, and a coronal plane of the medical image data.

In addition, the preset distance in reference to each of the horizontal plane, the sagittal plane, and the coronal plane may be determined by a user input.

According to an embodiment, the partial medical image data may be generated by rendering voxels having a value within a pre-defined Hounsfield Unit (HU) range in the ROI.

In addition, the pre-defined HU range may be determined based on a CT value of a specific tissue of the object.

In addition, the specific tissue may be arbitrarily determined by a user.

According to a further embodiment of the present invention, the partial medical image data may be generated by rendering voxels in the ROI with a light from a virtual light source at a predetermined point based on a position of the medical navigation device.

In this case, each pixel value $I(S_0, S_n)$ of the partial medical image data may be determined based on the following equation.

$$I(S_0, S_n) = \int_{S_0}^{S_n} \left\{ I_\lambda(x) e^{-\int_{S_0}^{x} \tau(t)dt} + K_{ref} \cdot L \cdot e^{-\int_{P_0}^{x} \tau(t)dt} \right\} dx$$

Herein, $S_0$ is a first voxel sampled by ray casting, $S_n$ is a last voxel sampled by ray casting, $I_\lambda(x)$ is a value of voxel x, $\tau(t)$ is an attenuation coefficient of voxel t, $K_{ref}$ is a reflection coefficient, $P_0$ is a position of the virtual light source, L is a brightness value of the virtual light source at $P_0$.

In this case, the $K_{ref}$ may be determined based on the following equation.

$$K_{ref} = \max(G(x) * V_{p0 \to x}, 0)$$

Herein, G (x) is a gradient vector at voxel x, and $V_{p0 \to x}$ is a direction vector from a position $P_0$ of the virtual light source to voxel x.

In addition, the medical image data may be set of voxels generated using the medical image of the object, and the partial medical image data is volume rendering data obtained by applying ray casting on voxels in the ROI.

Advantageous Effects

According to an embodiment of the present invention, the medical image and the surgical site image of the patient may be effectively rendered to provide convenience of surgery and medical diagnosis.

In addition, according to an embodiment of the present invention, it is possible to minimize the amount of computation required to render additional data included in the medical image.

In addition, according to an embodiment of the present invention, the operator can easily identify the anatomical structure of the patient thereby improving the convenience and concentration on the surgery.

DETAILED DESCRIPTION OF THE INVENTION

In the specification, up to date general terms are used considering functions in the present invention, but they may be changed depending on an intention of those skilled in the art, customs, and emergence of new technology. Further, in a specific case, there is a term arbitrarily selected by an applicant and in that case, a meaning thereof will be described in a corresponding description part of the invention. Accordingly, it should be revealed that a term used in the specification should be understood on not just a name of the term but a substantial meaning of the term and contents throughout the specification.

Throughout this specification and the claims that follow, when it is described that an element is "coupled" to another element, the element may be "directly coupled" to the other element or "electrically coupled" to the other element through a third element. Further, unless explicitly described to the contrary, the word "comprise" and variations such as "comprises" or "comprising", will be understood to imply the inclusion of stated elements but not the exclusion of any other elements. Moreover, limitations such as "or more" or "or less" based on a specific threshold may be appropriately substituted with "more than" or "less than", respectively.

Hereinafter, a medical image processing apparatus and a medical image processing method according to an exemplary embodiment of the present invention will be described with reference to the drawings. The image processing apparatus and the image processing method according to the embodiment of the present invention may be applied to a medical image of an object including a human body and an animal body. The medical image includes an X-ray image, a computed tomography (CT) image, a positron emission tomography (PET) image, an ultrasound image, and a magnetic resonance imaging (MRI), but the present invention is not limited thereto. In addition, in the present description, the term medical image data is used as a term in a broad sense including not only the medical image itself but also various types of data generated by rendering the medical image. According to an embodiment, the medical image data may refer to data obtained by performing volume rendering on the medical image. In addition, the medical image data may refer to a three-dimensional data set composed of a group of two-dimensional medical images. The value on a regular grid in the three-dimensional data set configured as described above is called a voxel. The medical image processing apparatus and the medical image processing method according to an embodiment of the present invention may generate or process an image provided by an endoscope and/or a medical navigation device.

Figure 1:
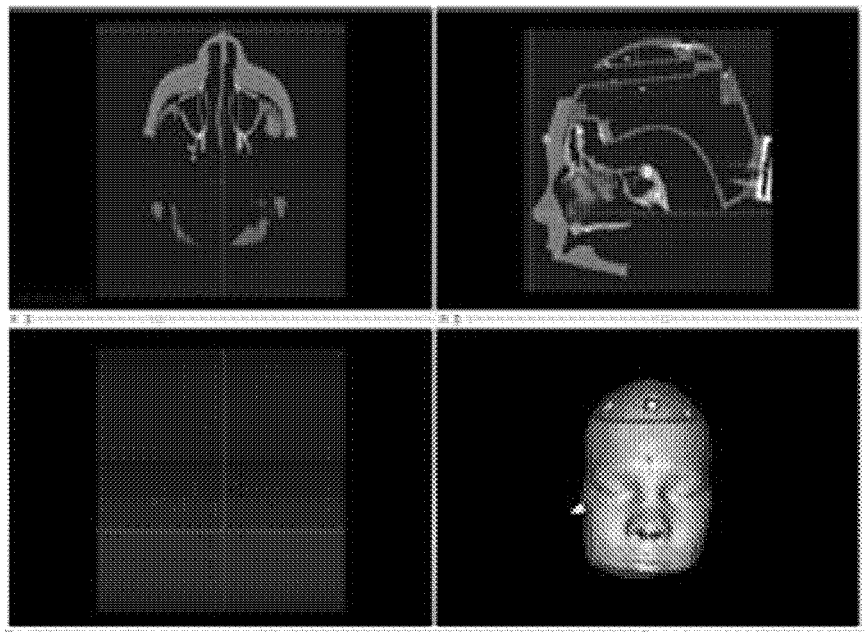
FIG. 1 illustrates an embodiment of an output image of a medical navigation device.
Figure 2:
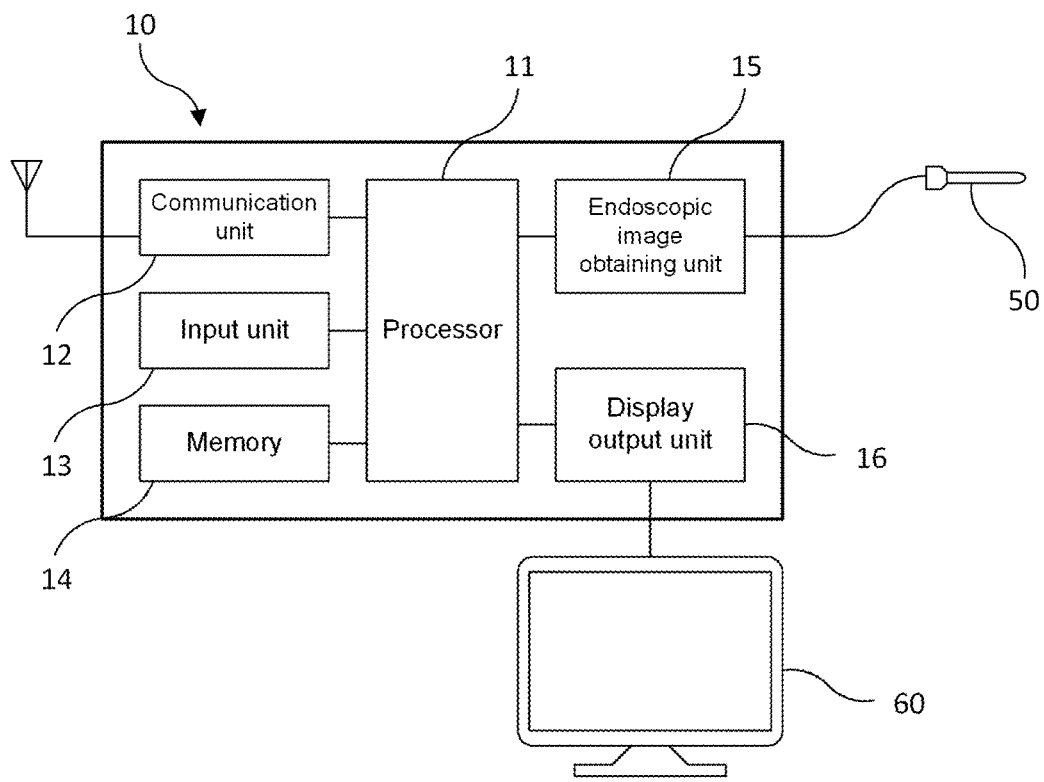
FIG. 2 is a block diagram of a medical image processing apparatus according to an embodiment of the present invention.

FIG. 2 is a block diagram of the medical image processing apparatus 10 according to an embodiment of the present invention. As illustrated, the medical image processing apparatus 10 according to an embodiment of the present invention may include a processor 11, a communication unit 12, an input unit 13, a memory 14, an endoscopic image obtaining unit 15, and a display output unit 16.

First, the communication unit 12 includes a wired/wireless communication module of various protocols for communicating with an external device. The input unit 13 includes various types of interfaces for receiving a user input for the medical image processing apparatus 10. According to an embodiment, the input unit 13 may include a keyboard, a mouse, a camera, a microphone, a pointer, a USB, a connection port with an external device, and the like, but the present invention is not limited thereto. The medical image processing apparatus may obtain a medical image of the object through the communication unit 12 and/or the input unit 13 in advance. The memory 14 stores a control program used in the medical image processing apparatus 10 and various data related thereto. For example, the memory 14 may store a previously obtained medical image of an object. In addition, the memory 14 may store medical image data generated by rendering the medical image of the object.

The endoscopic image obtaining unit 15 obtains an endoscopic image of a search area of an object captured by the endoscope 50. The endoscopic image obtaining unit 15 may be connected with the endoscope 50 by wire or wireless to receive an image from the endoscope 50.

The display output unit 16 outputs an image generated according to an embodiment of the present invention. That is, the display output unit 16 may output an augmented reality image together with the endoscopic image of the object as described below. In this case, the augmented reality image may include partial medical image data corresponding to the endoscopic image. The image output by the display output unit 16 may be displayed by the monitor 60 connected to the medical image processing apparatus 10.

The processor 11 of the present invention may execute various commands and programs and process data in the medical image processing apparatus 10. In addition, the processor 11 may control each unit of the preceding medical image processing apparatus 10 and control data transmission and reception between the units.

The medical image processing apparatus 10 illustrated in FIG. 2 is a block diagram according to an exemplary embodiment of the present invention, in which the separately displayed blocks logically distinguish elements of the apparatus. Therefore, the preceding elements of the medical image processing apparatus 10 may be mounted on one chip or on plural chips according to the design of the corresponding apparatus. In addition, some of the components of the medical image processing apparatus 10 illustrated in FIG. 2 may be omitted, and additional components may be included in the medical image processing apparatus 10.

Figure 3:
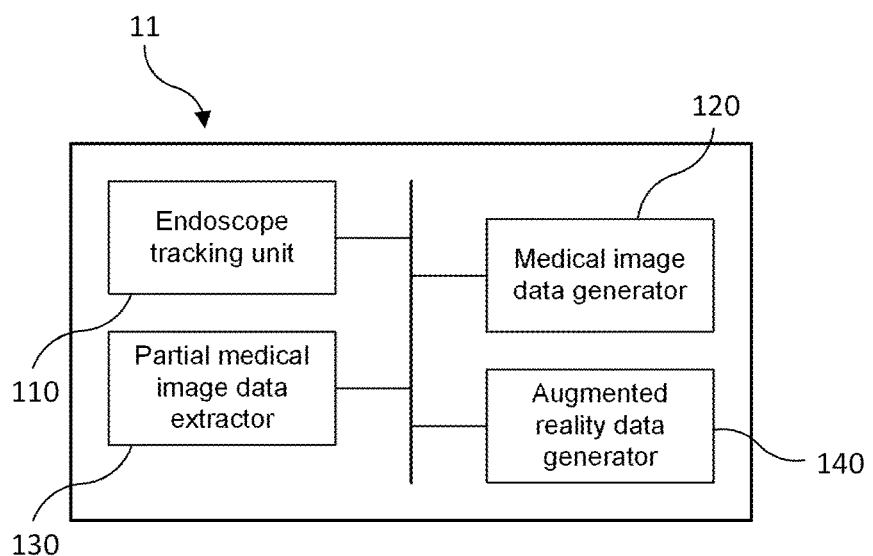
FIG. 3 is a more detailed block diagram of a processor of the medical image processing apparatus according to an embodiment of the present invention.

FIG. 3 is a more detailed block diagram of the processor 11 of the medical image processing apparatus 10 according to an embodiment of the present invention. As illustrated, the processor 11 of the medical image processing apparatus 10 according to an embodiment of the present invention may include an endoscope tracking unit 110, a medical image data generator 120, a partial medical image data extractor 130 and an augmented reality data generator 140.

The endoscope tracking unit 110 obtains position and direction information of the endoscope 50 that provides an endoscopic image to the medical image processing 10. More specifically, the endoscope tracking unit 110 obtains the position and direction information of the endoscope 50 (e.g., position and direction information of the endoscope camera) based on a medical image data coordinate system of the object. According to an embodiment of the present invention, the endoscope tracking unit 110 may track the position and direction of the endoscope 50 by analyzing the endoscopic image obtained through the endoscopic image obtaining unit 15. Specific embodiments thereof will be described later. Meanwhile, according to another embodiment of the present invention, the endoscope tracking unit 110 may include a separate endoscope tracking device to track the position and direction of the endoscope 50. When a 6 degree of freedom (DOF) tracking device is coupled to the endoscope 50, the endoscope tracking unit 110 may obtain the position and direction information of the endoscope 50 from the tracking device. When the registration process is performed on the position and direction information obtained from the tracking device, the position and direction information of the endoscope 50 in reference to the medical image data coordinate system may be obtained.

Next, the medical image data generator 120 renders a medical image of the object to generate medical image data. As described above, the medical image includes at least one of an X-ray image, a CT image, a PET image, an ultrasound image, and an MRI. According to an embodiment, the medical image data generator 120 may generate medical image data by performing volume rendering on the medical image of the object. In addition, the medical image data generator 120 may generate medical image data by synthesizing the medical image of the object and the user defined auxiliary data and performing volume rendering on the synthesized data. Specific embodiments thereof will be described later.

Next, the partial medical image extractor 130 extracts the partial medical image data to be displayed in augmented reality among the medical image data based on the computed position and direction information of the endoscope 50. More specifically, the partial medical image extractor 130 determines a target area (i.e., field of view) to be displayed in augmented reality among the medical image data based on the position and direction information of the endoscope 50. According to an embodiment of the present invention, the target area may be determined as a view frustum based on a specific focal length, a viewing angle, and a depth of the endoscope 50. Therefore, when the position and direction information of the endoscope 50 in reference to the medical image data coordinate system is obtained by the endoscope tracking unit 110, a target area to be represented in augmented reality within the medical image data may be determined. The partial medical image extractor 130 extracts partial medical image data corresponding to the target area determined as described above.

Next, the augmented reality data generator 140 renders the augmented reality image from the extracted partial medical image data. That is, the augmented reality data generator 140 may compose the partial medical image data with the endoscopic image and provide the partial medical image data as an augmented reality image for the endoscopic image.

Figure 4:
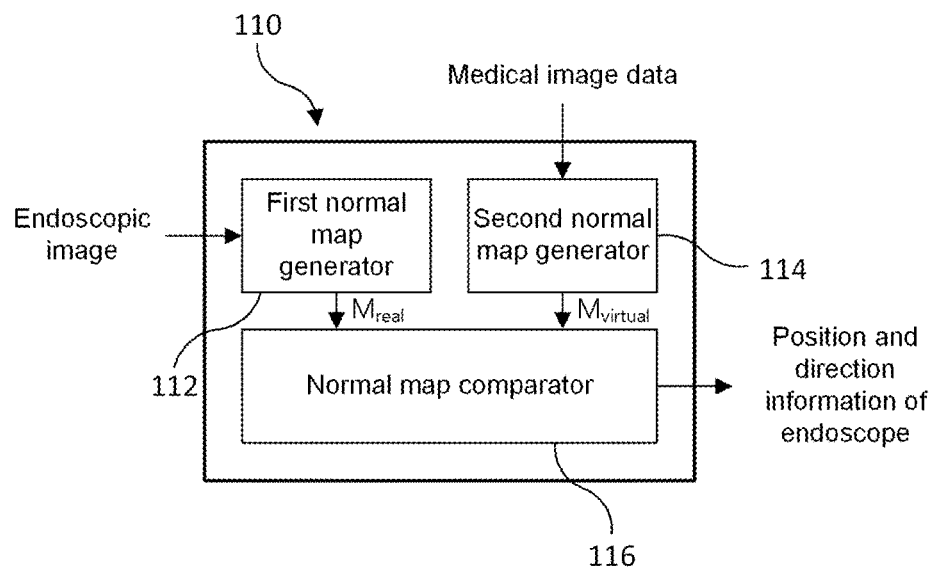
FIG. 4 is a block diagram of an endoscope tracking unit according to an embodiment of the present invention.

FIG. 4 is a block diagram of the endoscope tracking unit 110 according to an embodiment of the present invention. In order to match the endoscopic image and the augmented reality image in a meaningful form, the following information is required.

The position $P_f(X_f, Y_f, Z_f)$ of the endoscope 50 in reference to the medical image data coordinate system Direction vectors $V_{view}(X_v, Y_v, Z_v)$, $V_{up}(X_u, Y_u, Z_u)$ and $V_{right}(X_r, Y_r, Z_r)$ of the endoscope 50 in reference to the medical image data coordinate system Field of view (FOV) of the endoscope 50

Focal length of the endoscope 50

Depth of field (DOF) of the endoscope 50

Among the information, the viewing angle, focal length, and depth of field follow the fixed specifications of the endoscope lens (i.e., endoscope camera). Therefore, in order to determine a target area to be represented in augmented reality within the medical image data, position and direction information of the endoscope 50 should be obtained in real time.

According to an embodiment of the present invention, the endoscope tracking unit 110 may track the position and direction of the endoscope 50 via a separate endoscope tracking device. However, according to another embodiment of the present invention, the endoscope tracking unit 110 may track the position and direction of the endoscope 50 by comparing the endoscopic image and the medical image data. More specifically, the endoscope tracking unit 110 tracks the position and direction of the endoscope 50 by comparing a normal map based on an endoscopic image with plural candidate normal maps based on medical image data. The normal map maybe represented as two dimensional projection data of surface information of the search area.

Referring to FIG. 4, the endoscope tracking unit 110 may include a first normal map generator 112, a second normal map generator 114, and a normal map comparator 116. First, the first normal map generator 112 obtains an endoscopic image and generates the first normal map $M_{real}$ using the obtained endoscopic image. In general, an endoscopic image includes a spotlight type light source that is easy to find the direction of the light. In addition, the inside of the human body, which is observed by the endoscope, does not have a separate light source, and contains a lot of reflective saliva on the surface. As a result, the endoscopic image may maximize effects of highlight and shade. Therefore, according to an exemplary embodiment of the present invention, the first normal map generator 112 may analyze the intensity of light in the obtained endoscopic image to generate the first normal map $M_{real}$ in which the surface information of the three-dimensional search area is projected to the two-dimensional form. The first normal map $M_{real}$ generated by the first normal map generator 112 is transferred to the normal map comparator 116.

Figure 5:
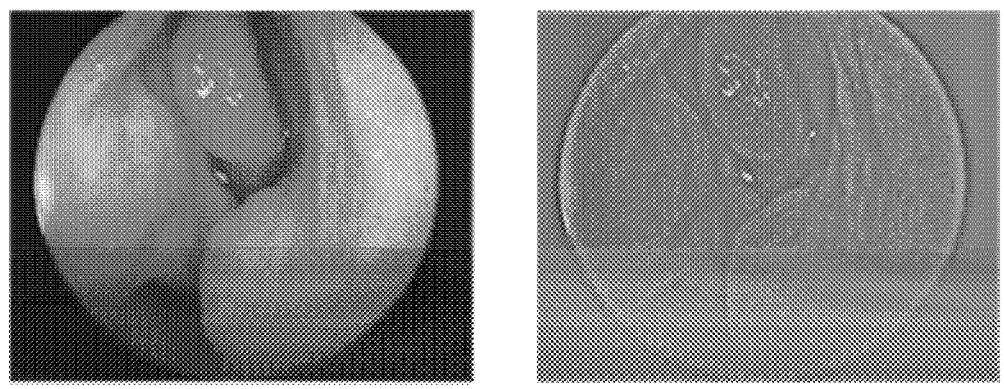
FIG. 5 illustrates an endoscopic image and a normal map generated using the same.

FIG. 5 illustrates an endoscopic image and a normal map generated using the same. FIG. 5(*a*) shows an endoscopic image obtained from the endoscope 50, and FIG. 5(*b*) shows a normal map generated using the endoscopic image. As shown in FIG. 5(*a*), the endoscopic image may clearly show highlights and shades on the curved surface. Accordingly, the medical image processing apparatus 10 of the present invention may generate a normal map as shown in FIG. 5(*b*) by analyzing the endoscopic image.

According to a further embodiment of the present invention, an endoscopic image to which structured light or patterned light is applied may be used to generate a more accurate first normal map $M_{real}$. In this case, the first normal map $M_{real}$ is obtained based on the reflection information of the structured light or the patterned light with respect to the search area of the object.

Returning to FIG. 4, the second normal map generator 114 obtains plural second normal maps $M_{virtual}$ from the medical image data. The user may determine the searching path of the endoscope for the medical image data in advance and store the information. According to an embodiment of the present invention, the second normal map generator 114 may divide the predetermined endo scope searching path by predetermined interval and generate a virtual endoscopic image corresponding to each divided point. The second normal map $M_{virtual}$ is obtained by using the virtual endoscopic image. The second normal map $M_{virtual}$ may be obtained from medical image data based on the position and direction information of the virtual endoscope (e.g., position and direction information of the virtual endoscope camera) with regard to the object. In this case, the direction information of the virtual endoscope may be determined based on a straight line connecting the start point (or a previous position) of the path of the virtual endoscope with the current position of the virtual endoscope. However, even if the virtual endoscope has the same position and the direction vector $V_{view}$, plural second normal maps $M_{virtual}$ are required in consideration of the rotation of the virtual endoscope in reference to the direction vector $V_{view}$. Therefore, according to an embodiment of the present invention, plural second normal maps $M_{virtual}$ may be generated according to predetermined angular interval with respect to one point may be obtained. The second normal map $M_{virtual}$ generated by the second normal map generator 114 is transferred to the normal map comparator 116.

The normal map comparator 116 compares the first normal map $M_{real}$ obtained from the endoscopic image with the plural second normal maps $M_{virtual}$ obtained from the medical image data to determine similarity. The position and direction information of the endoscope 50 in reference to the medical image data may be obtained based on the second normal map $M_{virtual}$ with highest similarity as a result of the similarity determination. According to a further embodiment of the present invention, in order to reduce the computing complexity of the similarity measure of the normal map, the normal map comparator 116 may preferentially compare the first normal map $M_{real}$ with the second normal maps $M_{virtual}$ within a preset range from the position and the direction of the endoscope 50 at a previous time point.

When the position and direction information of the endoscope 50 is obtained, the medical image processing apparatus 10 may extract partial medical image data to be displayed in augmented reality as described above, and render the extracted partial medical image data as an augmented reality image.

Figure 6:
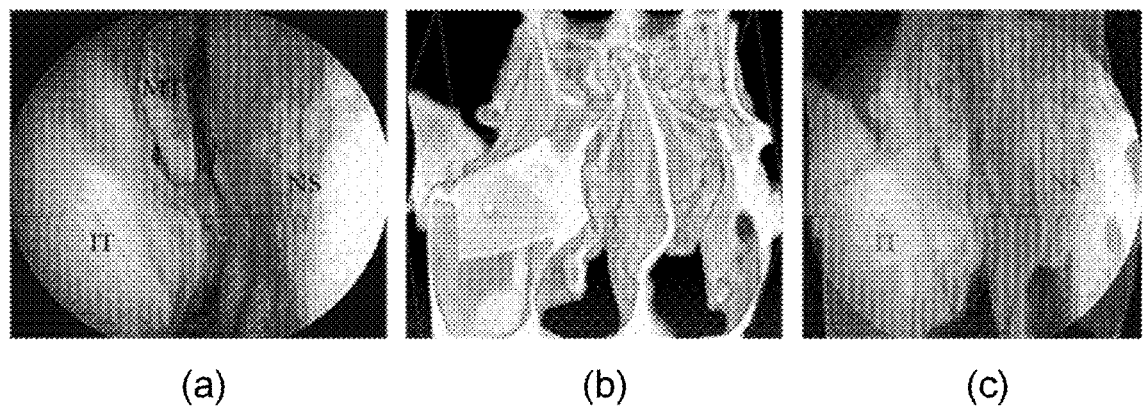
FIG. 6 illustrates an embodiment that medical image data is provided as an input of augmented reality image of endoscopic image.

FIG. 6 illustrates an embodiment that medical image data is provided as an augmented reality image for an endoscopic image. More specifically, FIG. 6(*a*) shows an endoscopic image, FIG. 6(*b*) shows partial medical image data, and FIG. 6(*c*) shows that partial medical image data is provided as an augmented reality image for the endoscopic image. When the position and direction information of the endoscope 50 in reference to the medical image data coordinate system is obtained according to the preceding embodiment of the present invention, the partial medical image data and the endoscopic image may be efficiently matched. Accordingly, information about the surgical site and the adjacent elements of the object may be intuitively identified by the operator.

Meanwhile, the medical image data to be represented in augmented reality may include various types of data. As described above, the medical image data may be data obtained by performing volume rendering on a medical image such as an X-ray image, a CT image, a PET image, an ultrasound image, and an MRI. According to a further embodiment of the present invention, the medical image data may include an image of a target organ (e.g., brain, eye, lung, heart, etc.) represented in a mesh form after segmentation in a medical image of the object. In addition, the medical image data may further include user defined auxiliary data. The auxiliary data includes planning information such as markers and paths inserted into the medical image before the surgery represented as a mesh. According to an embodiment of the present invention, the medical image processing apparatus 10 may perform volume rendering on the auxiliary data represented in the mesh form together with the medical image without performing surface rendering on it. More specifically, the medical image processing apparatus 10 may generate medical image data for augmented reality by synthesizing the auxiliary data with the medical image and performing volume rendering on the synthesized data.

Figure 7:
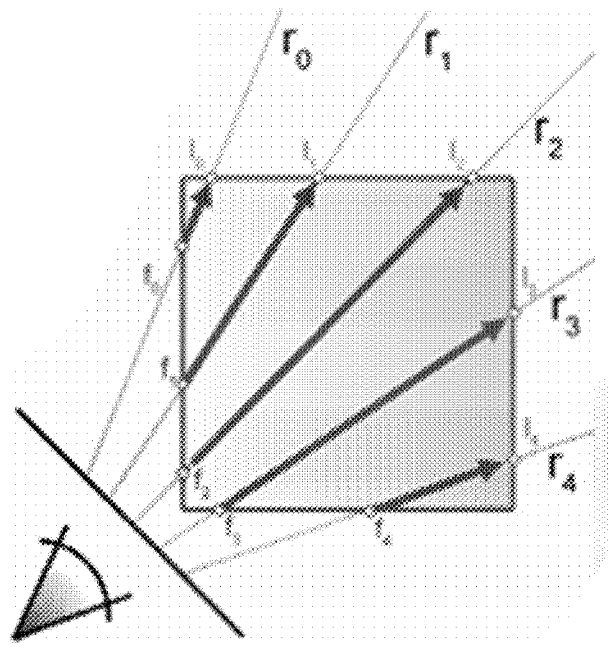
FIGS. 7 and 8 illustrate a volume rendering technique according to an embodiment of the present invention.
Figure 8:
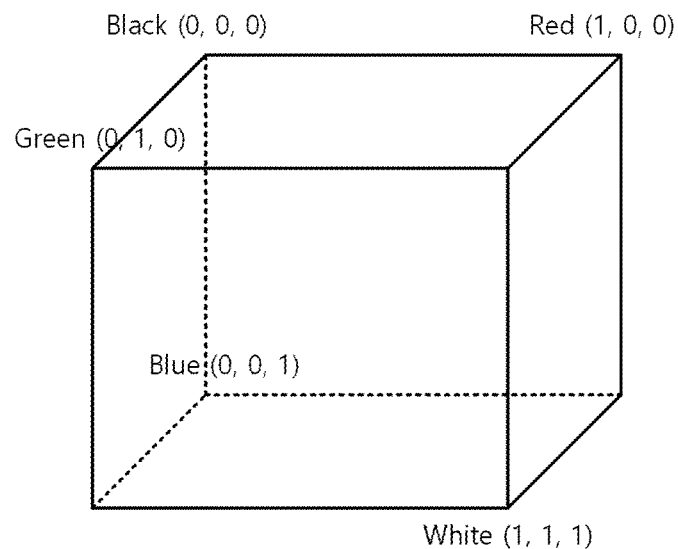

FIGS. 7 and 8 illustrate a volume rendering technique according to an embodiment of the present invention. The volume rendering is a technique for displaying two-dimensional projection images of three-dimensional sample data set. The general three-dimensional data set may be composed of a group of two-dimensional tomographic images collected from the preceding medical images. The images of the group may have a regular pattern and same number of pixels. The value on a regular grid in the three-dimensional data set configured as described above is called a voxel.

FIG. 7 illustrates a ray-casting technique that may be used in volume rendering. The ray casting method is defined as that the voxels constituting the volume have the property of being translucent and emitting light by themselves. The ray casting method accumulates voxel values sampled along with each ray $r_0, r_1, \ldots, r_4$ determined according to the line of sight of the user (or the position and direction of the camera) to obtain a rendering value (i.e., pixel value). In this case, the number of rays are determined according to the resolution of the resultant image. The color cube technique can be used to properly render three-dimensional volume data according to the line of sight of the user.

FIG. 8 illustrates a color cube used in volume rendering. As shown in FIG. 8, the color cube assigns black to the origin (0, 0, 0), assigns white to the vertex (1, 1, 1) diagonally opposite to the origin, and increases the intensity of the corresponding RGB value as the value of each coordinate increases within the cube. The RGB value for each coordinate is used as normalized texture sampling coordinate value.

In order to define the start point and the end point of each ray in the volume rendering, front and the rear face of color cube images with the same size (that is, the pixel size) may be generated. The value obtained at the same position of each of the two generated images becomes the start point and the end point of the ray corresponding to the position. When accumulating the values obtained by performing three-dimensional texture sampling of the medical image with a predetermined interval along with the ray from the start point to the end point, the intended volume rendering result may be obtained. The medical image data generator 120 of the medical image processing apparatus 10 according to an embodiment of the present invention may perform volume rendering and generate medical image data using the preceding method.

Figure 9:
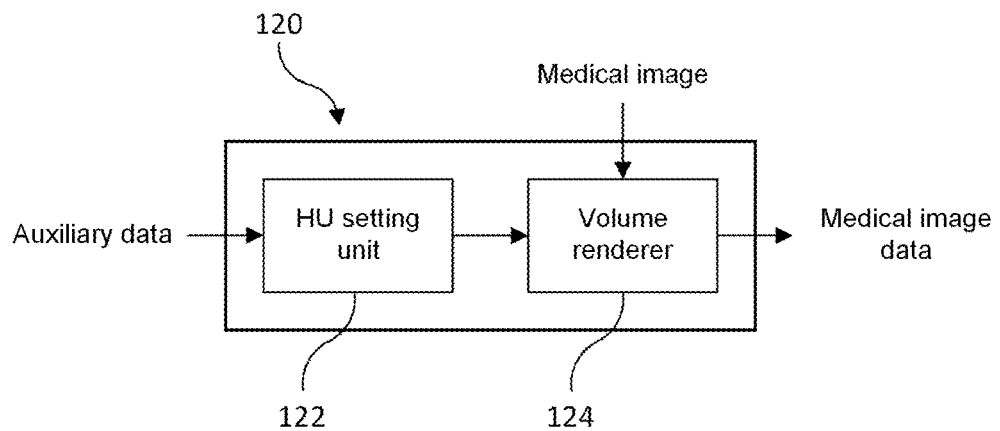
FIG. 9 is a block diagram of a medical image data generator according to an embodiment of the present invention.

FIG. 9 is a block diagram of the medical image data generator 120 according to an embodiment of the present invention. Referring to FIG. 9, the medical image data generator 120 according to an embodiment of the present invention may include a HU setting unit 122 and a volume renderer 124.

The volume renderer 124 receives the medical image of the object, and performs volume rendering on the received medical image to generate medical image data. As described above, the medical image may include at least one of an X-ray image, a CT image, a PET image, an ultrasound image, and an MRI, but the present invention is not limited thereto. According to a further embodiment of the present invention, the volume renderer 124 may perform volume rendering on the user defined auxiliary data as well as the medical image of the object. The auxiliary data may represent arbitrary information whose size and position are defined in reference to a medical image coordinate system such as a path, a critical zone, and the like previously prepared by the user.

In general, the auxiliary data may be defined in the form of a triangle mesh and drawn separately from the medical image and then synthesized. However, according to an exemplary embodiment of the present invention, the volume rendering may be performed after synthesizing previously prepared auxiliary data with the medical image. In order to perform the volume rendering of the auxiliary data together with the medical image, the auxiliary data may be represented as voxels having a predetermined range of values.

In the case of CT, which is the most widely used medical image, the CT values of each component of the human body are shown in Table 1 below. In this case, the unit of each value is Hounsfield Unit (HU).

TABLE 1

| Tissue | CT Number (HU) |
| --- | --- |
| Bone | +1000 |
| Liver | 40~60 |
| White matter | −20~−30 |
| Gray matter | −37~−45 |
| Blood | 40 |
| Muscle | 10~40 |
| Kidney | 30 |
| Cerebrospinal Fluid (CSF) | 15 |
| Water | 0 |
| Fat | −50~−100 |
| Air | ~1000 |

Data according to digital imaging and communications in medicine (DICOM), which is the medical imaging standard, uses 2 bytes per pixel. Thus, the range of values each pixel can have is $2^{16}$, ranging from −32768 to 32767. Foreign substances such as implants may be inserted into the human body, but they are substituted with appropriate values during the reconstruction process so that values outside the range of +/−1000 HU are not used in the CT.

Therefore, according to an embodiment of the present invention, the auxiliary data may be represented as a voxel having a value outside the pre-defined HU range. In this case, the pre-defined HU range may be from −1000 HU to +1000 HU, but the present invention is not limited thereto. The HU setting unit 122 may substitute the voxel value corresponding to the position occupied by the auxiliary data in the medical image data with a value outside the range of +/−1000 HU. The volume renderer 124 obtains the voxel data substituted by the value outside the pre-defined HU range from the HU setting unit 122 and performs volume rendering on it together with the medical image. When performing volume rendering of the auxiliary data together with the medical image, the amount of computation required to render additional data included in the medical image may be minimized.

According to a further embodiment of the present invention, the range outside the pre-defined HU range may include the first HU range exceeding the first threshold and the second HU range below the second threshold. In this case, the first threshold may be +1000 HU, and the second threshold may be −1000 HU. The HU setting unit 122 may set a value of the first HU range and a value of the second HU range to represent different types of auxiliary data. For example, the value of the first HU range may represent marker information set by the user, and the value of the second HU range may represent path information. According to another embodiment, the value of the first HU range may represent path information, and the value of the second HU range may represent critical zone information. By representing the auxiliary data as voxels having different ranges of values, the user may easily identify different types of auxiliary data. The above-mentioned classification criteria of the auxiliary data type and the HU range allocation method are illustrative of the present invention, and the present invention is not limited thereto.

Figure 10:
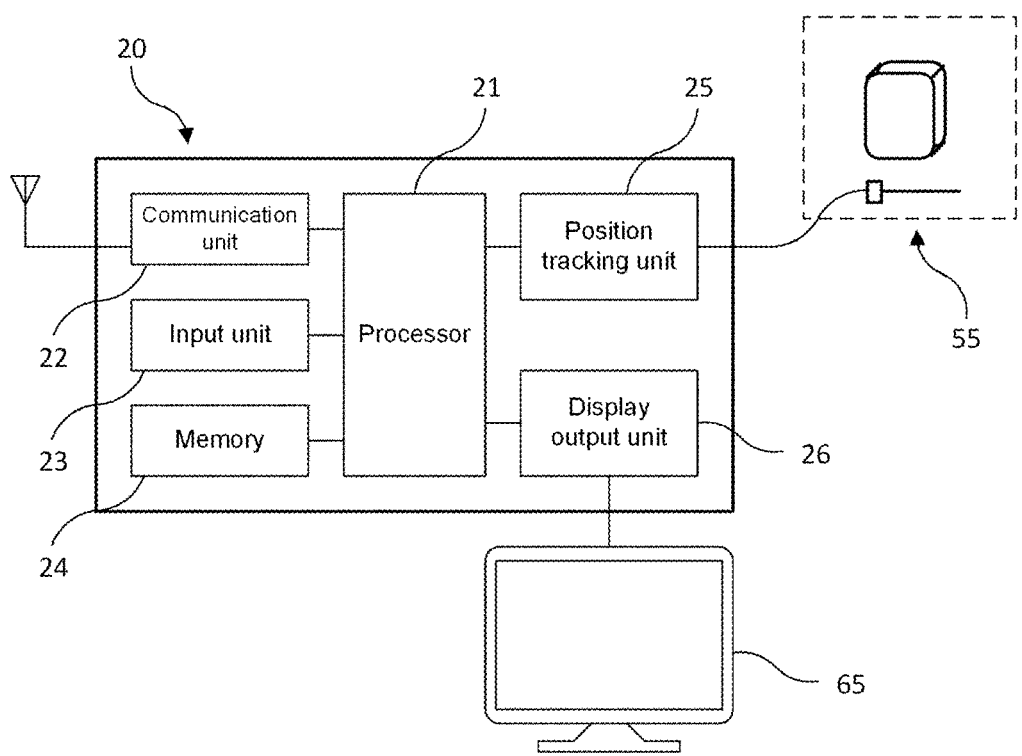
FIG. 10 is a block diagram of a medical image processing apparatus according to another exemplary embodiment of the present invention.

FIG. 10 is a block diagram of a medical image processing apparatus 20 according to another embodiment of the present invention. As illustrated, the medical image processing apparatus 20 according to an embodiment of the present invention includes a processor 21, a communication unit 22, an input unit 23, a memory 24, a position tracking unit 25, and a display output unit 26.

First, the communication unit 22 includes a wired/wireless communication module of various protocols for communicating with an external device. The input unit 23 includes various types of interfaces for receiving a user input for the medical image processing apparatus 20. According to an embodiment, the input unit 23 may include a keyboard, a mouse, a camera, a microphone, a pointer, a USB, a connection port with an external device, and the like, but the present invention is not limited thereto. The medical image processing apparatus may obtain a medical image of the object through the communication unit 22 and/or the input unit 23 in advance. The memory 24 stores a control program used in the medical image processing apparatus 10 and various data related thereto. For example, the memory 24 may store a previously obtained medical image of an object. In addition, the memory 24 may store medical image data generated by rendering a medical image of the object.

The position tracking unit 25 obtains position information of the medical navigation device 55 in the object. In the embodiment of the present invention, the medical navigation device 55 may include various kinds of surgical navigation devices. An optical position tracking method or an electromagnetic position tracking method may be used for position tracking of a medical navigation device, but the present invention is not limited thereto. If the position information obtained from the medical navigation device 55 is not matched with the medical image data of the object, the position tracking unit 25 may perform a matching process to generate position information of the medical navigation device 55 in reference to the medical image data. The position tracking unit 25 may be connected to the medical navigation device 55 by wire or wireless to receive position information from the medical navigation device 55.

The display output unit 26 outputs an image generated according to an embodiment of the present invention. That is, the display output unit 26 may output medical image data corresponding to the region of interest with respect to the object as described below. The image output by the display output unit 26 may be displayed by the monitor 65 connected to the medical image processing apparatus 20.

The processor 21 of the present invention may execute various commands or programs and process data in the medical image processing apparatus 20. In addition, the processor 21 may control each unit of the preceding medical image processing apparatus 20 and control data transmission and reception between the units.

The medical image processing apparatus 20 illustrated in FIG. 10 is a block diagram according to an exemplary embodiment of the present invention, in which the separately displayed blocks logically distinguish elements of the apparatus. Therefore, the preceding elements of the medical image processing apparatus 20 may be mounted on one chip or on plural chips according to the design of the corresponding apparatus. In addition, some of the components of the medical image processing apparatus 20 illustrated in FIG. 10 may be omitted, and additional components may be included in the medical image processing apparatus 20.

Figure 11:
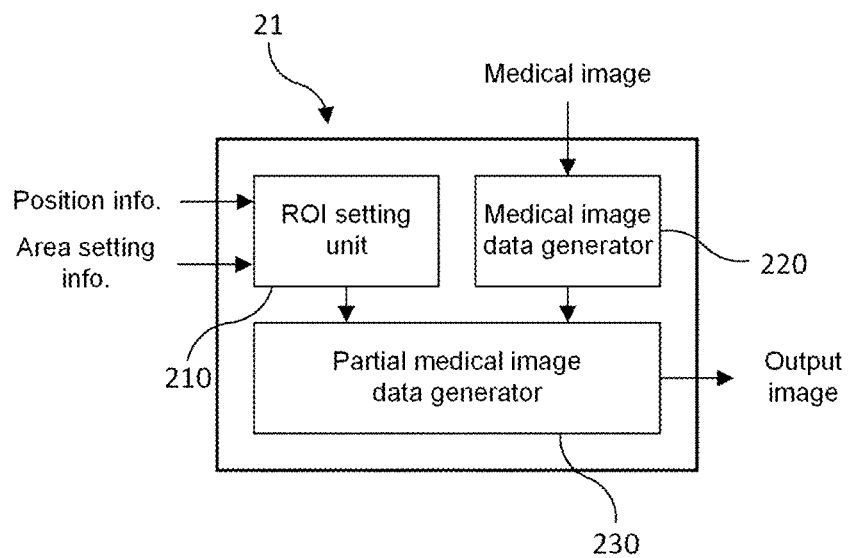
FIG. 11 is a more detailed block diagram of a processor of the medical image processing apparatus according to another embodiment of the present invention.

FIG. 11 is a more detailed block diagram of a processor 21 of the medical image processing apparatus 20 according to another embodiment of the present invention. As illustrated, the processor 21 of the medical image processing apparatus 20 according to another embodiment of the present invention may include a region of interest (ROI) setting unit 210, a medical image data generator 220, and a partial medical image data generator 230.

The ROI setting unit 210 sets the ROI of the user with respect to the object. More specifically, the ROI setting unit 210 receives the position information of the medical navigation device 55 from the position tracking unit 25 and sets the ROI based on the position information. According to an embodiment of the present invention, the ROI is set based on an area within a preset distance from the position of the medical navigation device 55 in reference to at least one of the horizontal plane, the sagittal plane, and the coronal plane of the medical image data. As such, the ROI may be set as a three-dimensional region including an area within a preset distance from a plane based on the position of the medical navigation device 55. Therefore, the ROI may be set as a slab having a thickness based on the preset distance. According to an embodiment, the ROI may be set in reference to at least one of the horizontal plane, the sagittal plane, and the coronal plane of the medical image data. To this end, the ROI setting unit 210 may receive in advance, as a user input, information on a preset distance (i.e., area setting information) in reference to each of the horizontal plane, the sagittal plane, and the coronal plane. The ROI setting unit 210 sets an ROI by cropping an area included, from the position of the medical navigation device 55, within the first distance in reference to the horizontal plane, within the second distance in reference to the sagittal plane, and/or within the third distance in reference to the coronal plane. If the user does not input area setting information on at least one reference plane among the horizontal plane, the sagittal plane and the coronal plane, the ROI setting unit 210 may not perform cropping in reference to the plane. The ROI information obtained by the ROI setting unit 210 is transferred to the partial medical image data generator 230.

Next, the medical image data generator 220 renders a medical image of the object to generate medical image data. As described above, the medical image includes at least one of an X-ray image, a CT image, a PET image, an ultrasound image, and an MRI. The medical image data may refer to voxels generated using the medical image of the object. However, the present invention is not limited thereto, and the medical image data may refer to data obtained by volume rendering the medical image of an object.

Next, the partial medical image data generator 230 extracts and renders medical image data of a portion corresponding to the ROI among the medical image data of the object. More specifically, the partial medical image data generator 230 may perform volume rendering by selectively ray casting voxels of the ROI. Accordingly, by preventing objects other than the ROI from overlapping with objects of the ROI within the object, the operator can easily identify the anatomical structure of the object.

According to an embodiment of the present invention, the partial medical image data generator 230 may generate volume rendering data in various ways. According to an embodiment, the partial medical image data generator 230 may generate volume rendering data by performing ray casting on all of the voxels included in the ROI.

According to another embodiment of the present invention, the partial medical image data generator 230 may generate volume rendering data by selectively performing ray casting on voxels having a value within a pre-defined HU range in the ROI. In this case, the pre-defined HU range may be determined based on the CT value of a specific tissue of the object. In addition, the specific tissue for performing the volume rendering may be selected by the user. In this way, volume rendering data may be generated by selectively performing ray casting only on voxels corresponding to a specific tissue selected by a user setting in the ROI.

As explained through Table 1, the range of CT values of each component of a human body is predetermined. If the user wants to selectively check only gray matter in the ROI with respect to the object, the user may input an arbitrary value within the CT value range of −37 to −45 or input a CT value range including the corresponding range through the input unit 23. In addition, the user may input a selection for gray matter among predetermined tissues of the object through the input unit 23. The partial medical image data generator 230 may generate volume rendering data by selectively performing ray casting only on voxels corresponding to the gray matter within the ROI of the object based on the user input.

According to another exemplary embodiment of the present invention, the partial medical image data generator 230 may generate partial medical image data by rendering voxel values of an ROI when light is emitted from a virtual light source at a predetermined point based on the position of the medical navigation device 55. More specifically, the partial medical image data generator 230 may assume that a virtual light source exists at a predetermined point based on the position of the medical navigation device 55, and set voxel values of an ROI when light is emitted from the virtual light source. The partial medical image data generator 230 may generate volume rendering data by performing ray casting on the voxels set as described above. Specific embodiments thereof will be described later.

The partial medical image data generated by the partial medical image data generator 230 may be provided as an output image of the display output unit 26.

Figure 12:
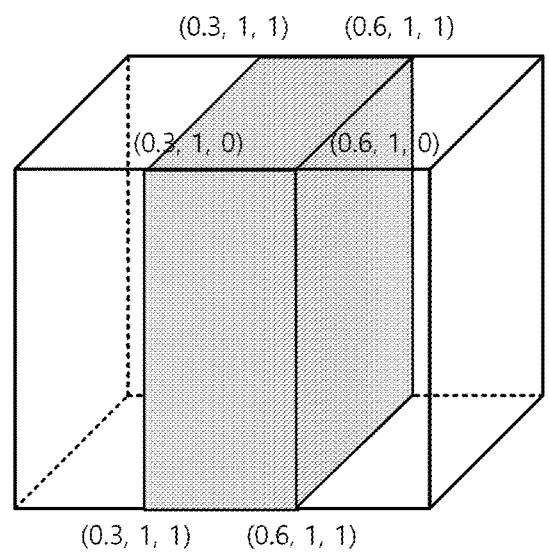
FIG. 12 illustrates an example of defining region of interest with respect to an object.
Figure 13:
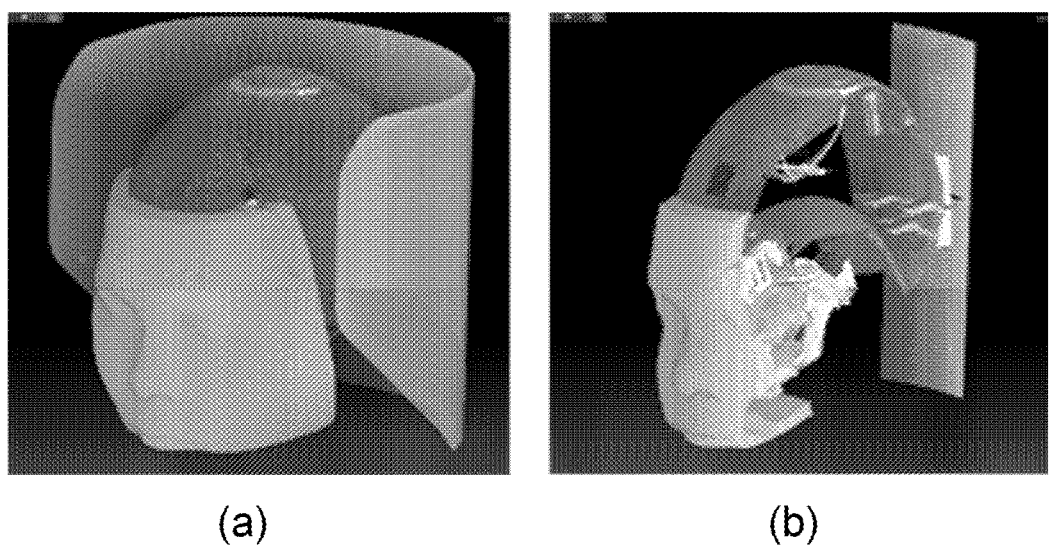
FIG. 13 illustrates partial medical image data corresponding to the region of interest defined in an embodiment of FIG. 12.

FIG. 12 illustrates an example of defining an ROI with respect to an object. Referring to FIG. 12, in the color cube for performing the volume rendering, an area included within a specific distance in reference to the sagittal plane is set as the ROI. FIG. 13 illustrates partial medical image data corresponding to the ROI defined as described above. More specifically, FIG. 13(a) illustrates volume rendering data of an object included in a cube, and FIG. 13(b) illustrates volume rendering data corresponding to the ROI defined in an embodiment of FIG. 12. As shown in FIG. 13(b), according to the ROI setting of the user, only an area included within a specific distance in reference to the sagittal plane of the object may be volume-rendered and displayed.

Figure 14:
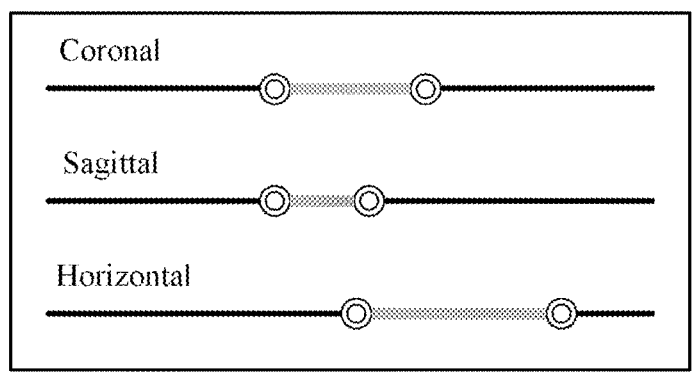
FIG. 14 illustrates an embodiment of user interface for defining a region of interest with respect to an object.

FIG. 14 illustrates an embodiment of a user interface for defining an ROI of an object. Referring to FIG. 14, the user interface may receive information (i.e., area setting information) on a preset distance in reference to each of the horizontal plane, the sagittal plane, and the coronal plane of the object from the user. The ROI is set based on an area within a preset distance from the position of the medical navigation device 55 in reference to at least one of the horizontal plane, the sagittal plane, and the coronal plane of the medical image data. According to an embodiment of the present invention, the position information of the medical navigation device 55 obtained from the position tracking unit 25 may be displayed in a specific coordinate on the slide bar for each reference plane in the user interface. The user may set a reference distance to be included in the ROI based on the coordinates displayed on each slide bar. The ROI setting unit 210 receives at least one of first distance information in reference to the horizontal plane, second distance information in reference to the sagittal plane, and third distance information in reference to the coronal plane through the user interface. The ROI setting unit 210 sets an ROI by cropping an area included, from the position of the medical navigation device 55, within the first distance in reference to the horizontal plane, within the second distance in reference to the sagittal plane, and/or within the third distance in reference to the coronal plane.

Figure 15:
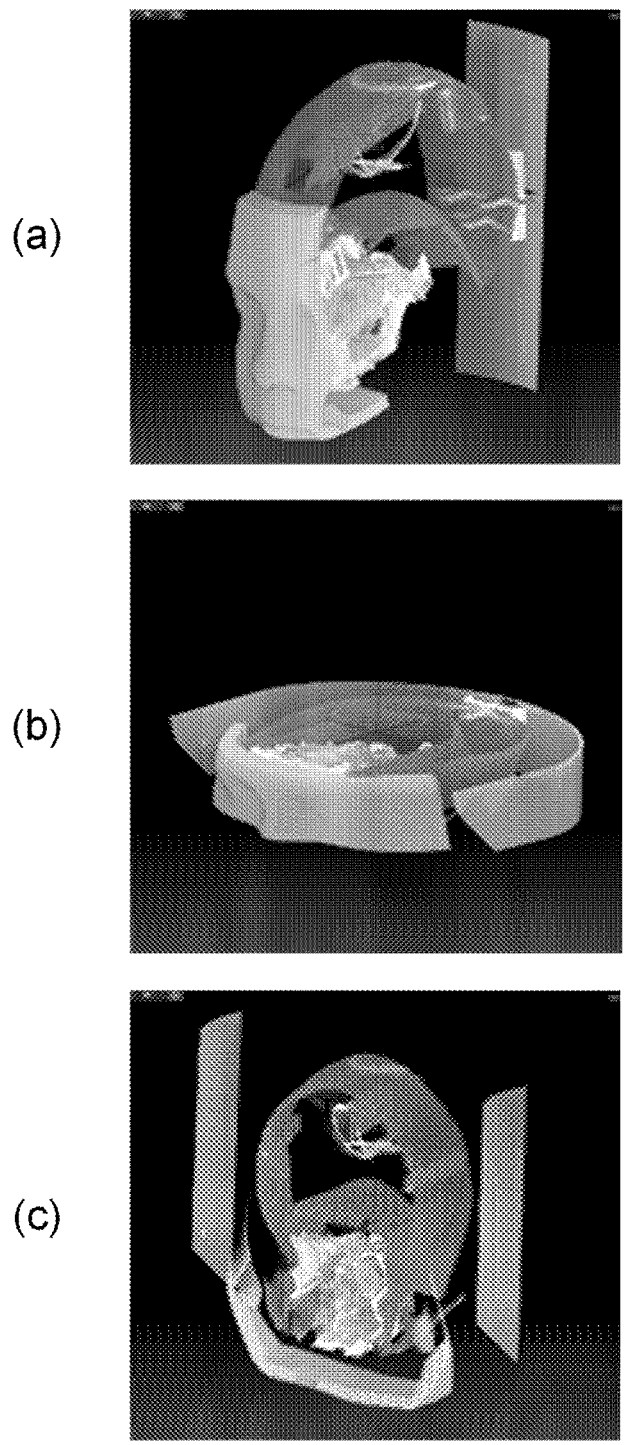
FIGS. 15 and 16 illustrate partial medical image data corresponding to various regions of interest.
Figure 16:
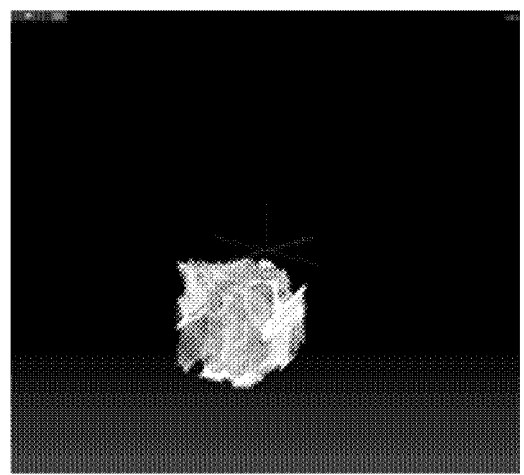

FIGS. 15 and 16 illustrate partial medical image data corresponding to various regions of interest. FIG. 15(a) illustrates a case where the ROI is set based on the sagittal plane of the object, FIG. 15(b) illustrates a case where the ROI is set based on the horizontal plane of the object, and FIG. 15(c) illustrates a case where the ROI is set based on the coronal plane of the object, respectively. In addition, FIG. 16 illustrates a case where the ROI is set based on all of the sagittal plane, the horizontal plane, and the coronal plane of the object. As described above, according to the embodiment of the present invention, the ROI may be set in various forms according to the user setting, and only the medical image corresponding to the ROI may be selectively rendered and provided to the user.

Meanwhile, in the above embodiments, it is illustrated that the ROI is set based on the horizontal plane, sagittal plane, and coronal plane of the medical image data, but the present invention is not limited thereto. In the present invention, the ROI may be set with respect to any reference axis or reference plane of the medical image data.

Figure 17:
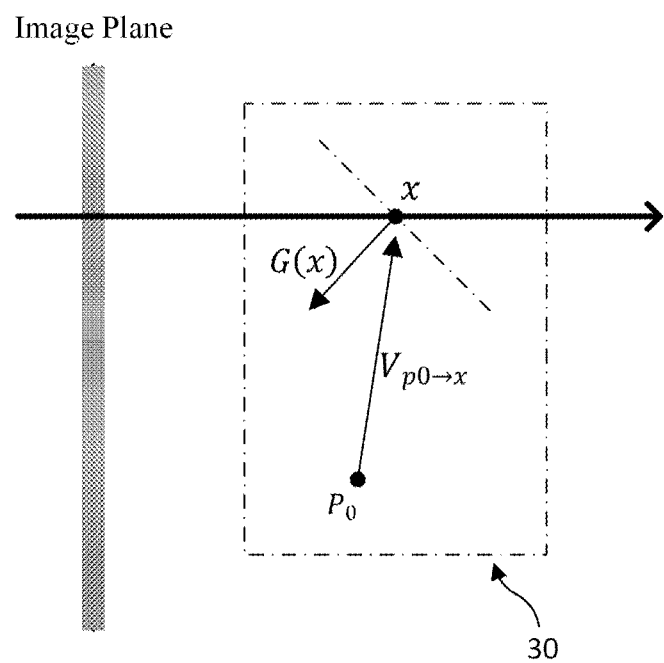
FIG. 17 illustrates a method of generating partial medical image data according to an additional embodiment of the present invention.

FIG. 17 illustrates a method of generating partial medical image data according to an additional embodiment of the present invention. As described above, the partial medical image data generator 230 may generate the partial medical image data by rendering voxel values of the ROI under an assumption that light is emitted from a virtual light source at a predetermined point for a special effect on the ROI 30.

First, each pixel value $I(S_0, S_n)$ of the volume rendering data using the general ray casting method may be expressed by Equation 1 below.

$$I(S_0, S_n) = \int_{S_0}^{S_n} \left\{ I_\lambda(x) e^{-\int_{S_0}^{x} \tau(t)dt} + K_{ref} \cdot L \cdot e^{-\int_{P_0}^{x} \tau(t)dt} \right\} dx \quad \text{[Equation 1]}$$

Here, $S_0$ denotes the first voxel sampled by ray casting, and $S_n$ denotes the last voxel sampled by ray casting. In addition, $I_\lambda(x)$ denotes a value of the voxel x (or an intensity of the voxel x), and $$e^{-\int_{S_0}^{x} \tau(f)dt}$$

denotes a transparency accumulated from the first voxel $S_0$ to the current voxel x. $\tau(t)$ denotes an attenuation coefficient of the voxel t.

According to an embodiment of the present invention, it is assumed that a virtual light source exists at a predetermined point $P_0$ based on the position of the medical navigation device 55, and the voxel values of the ROI 30 may be set when the light is emitted from the virtual light source. In this case, the value $I'_\lambda(x)$ of the voxel x may be expressed by Equation 2 below.

$$I'_\lambda(x) = I_\lambda(x) + R(x) \quad \text{[Equation 2]}$$

Here, $R(x)$ is a voxel value adjusted by the light emitted from the virtual light source and may be defined as in Equation 3 below.

$$R(x) = K_{ref} \cdot L \cdot e^{-\int_{P_0}^{x} \tau(t)dt} \quad \text{[Equation 3]}$$

Here, $K_{ref}$ denotes a reflection coefficient, $P_0$ denotes a position of the virtual light source, and L denotes a brightness value of the virtual light source at $P_0$, respectively. According to an embodiment of the present invention, the reflection coefficient $K_{ref}$ may be determined as in Equation 4 below.

$$K_{ref} = \max(G(x) * V_{p0 \to x}, 0) \quad \text{[Equation 4]}$$

Here, $G(x)$ denotes a gradient vector in the voxel x, and $V_{p0 \to x}$ denotes the direction vector from the position P0 of the virtual light source to the voxel x, respectively. According to an embodiment, the gradient vector $G(x)$ may be defined as a normal to a reference plane in which peripheral voxel values change most with respect to the voxel x.

Therefore, according to an embodiment of the present invention, each pixel value $I(S_0, S_n)$ of the partial medical image data may be determined based on Equation 5 below.

$$I(S_0, S_n) = \int_{S_0}^{S_n} \left\{ I_\lambda(x) e^{-\int_{S_0}^{x} \tau(t)dt} + K_{ref} \cdot L \cdot e^{-\int_{P_0}^{x} \tau(t)dt} \right\} dx \quad \text{[Equation 5]}$$

The partial medical image data generator 230 sets the volume rendering data generated as above as the partial medical image data. According to such an additional embodiment of the present invention, the effect may be as if an illumination is inserted into or around the ROI. When an illumination is inserted into or around the ROI, the stereoscopic effect of the ROI may be maximized due to the shadow effect on the ROI, and the user's identification of the ROI may be increased.

The description of the present invention is used for exemplification and those skilled in the art will be able to understand that the present invention can be easily modified to other detailed forms without changing the technical idea or an essential feature thereof. Thus, it is to be appreciated that the embodiments described above are intended to be illustrative in every sense, and not restrictive. For example, each component described as a single type may be implemented to be distributed and similarly, components described to be distributed may also be implemented in an associated form.

The scope of the present invention is represented by the claims to be described below rather than the detailed description, and it is to be interpreted that the meaning and scope of the claims and all the changes or modified forms derived from the equivalents thereof come within the scope of the present invention.

The invention claimed is:

1. A medical image processing apparatus for a medical navigation device, comprising:
 a position tracker configured to obtain position information of the medical navigation device within an object;
 a memory configured to store medical image data generated based on a medical image of the object; and
 a processor configured to set a region of interest (ROI) based on position information of the medical navigation device in reference to the medical image data, and generate partial medical image data corresponding to the ROI,
 wherein the ROI is set to a three-dimensional region including a region within a preset distance from a reference plane based on a position of the medical navigation device,
 wherein the reference plane is set based on at least one of a horizontal plane, a sagittal plane, and a coronal plane of the medical image data,
 wherein the partial medical image data is generated by rendering voxels in the ROI with a light from a virtual light source at a predetermined point based on a position of the medical navigation device, and
 wherein each pixel value $I(S_0, S_n)$ of the partial medical image data is determined based on the following equation:

$$I(S_0, S_n) = \int_{S_0}^{S_n} \left\{ I\lambda(x) e^{-\int_{S_0}^{x} \tau(t)dt} + K_{ref} \cdot L \cdot e^{-\int_{P_0}^{x} \tau(t)dt} \right\} dx$$

herein $S_0$ is a first voxel sampled by ray casting $S_n$ is a last voxel sampled by ray casting, $I\lambda(x)$ is a value of voxel x, $\tau(t)$ is an attenuation coefficient of voxel t, $K_{ref}$ is a reflection coefficient, $P_0$ is a position of the virtual light source, L is a brightness value of the virtual light source at $P_0$.

2. The apparatus of claim 1, wherein the preset distance in reference to each of the horizontal plane, the sagittal plane, and the coronal plane is determined by a user input.

3. The apparatus of claim 1, wherein the partial medical image data is generated by rendering voxels in the ROI having a value within a pre-defined Hounsfield Unit (HU) range.

4. The apparatus of claim 3, wherein the pre-defined HU range is determined based on a CT value of a specific tissue of the object.

5. The apparatus of claim 4, wherein the specific tissue is determined by a selection of a user.

6. The apparatus of claim 1, wherein the $K_{ref}$ is determined based on the following equation:

$$K_{ref} = \max(G(x) * V_{p0 \to x}, 0)$$

herein G (x) is a gradient vector at voxel x, and $V_{p0 \to x}$ is a direction vector from a position $P_0$ of the virtual light source to voxel x.

7. The apparatus of claim 1, wherein the medical image data is set of voxels generated using the medical image of the object, and the partial medical image data is volume rendering data obtained by applying ray casting on voxels in the ROI.

8. A medical image processing method for a medical navigation device, comprising:
 obtaining position information of the medical navigation device within an object;
 storing medical image data generated based on a medical image of the object;
 setting a region of interest (ROI) based on position information of the medical navigation device in reference to the medical image data; and
 generating partial medical image data corresponding to the ROI,
 wherein the ROI is set to a three-dimensional region including a region within a preset distance from a reference plane based on a position of the medical navigation device,
 wherein the reference plane is set based on at least one of a horizontal plane, a sagittal plane, and a coronal plane of the medical image data, and
 wherein the partial medical image data is generated by rendering voxels in the ROI with a light from a virtual light source at a predetermined point based on a position of the medical navigation device, and
 wherein each pixel value $I(S_0, S_n)$ of the partial medical image data is determined based on the following equation:

$$I(S_0, S_n) = \int_{S_0}^{S_n} \left\{ I\lambda(x) e^{-\int_{S_0}^{x} \tau(t)dt} + K_{ref} \cdot L \cdot e^{-\int_{P_0}^{x} \tau(t)dt} \right\} dx$$

herein $S_0$ is a first voxel sampled by ray casting $S_n$ is a last voxel sampled by ray casting, $I\lambda(x)$ is a value of voxel x, $\tau(t)$ is an attenuation coefficient of voxel t, $K_{ref}$ is a reflection coefficient, $P_0$ is a position of the virtual light source, L is a brightness value of the virtual light source at $P_0$.

9. The method of claim 8, wherein the preset distance in reference to each of the horizontal plane, the sagittal plane, and the coronal plane is determined by a user input.

10. The method of claim 8, wherein the partial medical image data is generated by rendering voxels in the ROI having a value within a pre-defined Hounsfield Unit (HU) range.

11. The method of claim 10, wherein the pre-defined HU range is determined based on a CT value of a specific tissue of the object.

12. The method of claim 11, wherein the specific tissue is determined by a selection of a user.

13. The method of claim 8, wherein the $K_{ref}$ is determined based on the following equation:

$$K_{ref} = \max(G(x) * V_{p0 \to x}, 0)$$

herein, G (x) is a gradient vector at voxel x, and $V_{p0 \to x}$ is a direction vector from a position $P_0$ of the virtual light source to voxel x.

14. The method of claim 8, wherein the medical image data is set of voxels generated using the medical image of the object, and the partial medical image data is volume rendering data obtained by applying ray casting on voxels in the ROI.

* * * * *